United States Patent [19]
Horiuchi et al.

[11] Patent Number: 6,017,911
[45] Date of Patent: Jan. 25, 2000

[54] PYRIDONECARBOXYLIC ACID DERIVATIVES AND INTERMEDIATES FOR THE SYNTHESIS THEREOF

[75] Inventors: Nobuhiko Horiuchi, Souraku-gun; Takenori Yonezawa, Neyagawa; Katsumi Chiba, Osaka; Hiroaki Yoshida, Sanda, all of Japan

[73] Assignee: Dainippon Pharmaceutical Co., Ltd., Osaka, Japan

[21] Appl. No.: 09/125,765

[22] PCT Filed: Feb. 25, 1997

[86] PCT No.: PCT/JP97/00530

§ 371 Date: Aug. 25, 1998

§ 102(e) Date: Aug. 25, 1998

[87] PCT Pub. No.: WO97/31919

PCT Pub. Date: Sep. 4, 1997

[30] Foreign Application Priority Data

Feb. 27, 1996 [JP] Japan .................................. 8-067235

[51] Int. Cl.$^7$ ........................ A61K 31/47; A61K 31/535; C07D 215/56; C07D 471/04; C07D 491/48
[52] U.S. Cl. .................................... 514/229.5; 514/230.2; 514/229.2; 514/300; 514/312; 544/66; 544/101; 546/123; 546/156; 548/453
[58] Field of Search ..................................... 546/123, 156; 514/300, 312, 230.5, 229.2; 544/101, 66; 548/453

[56] References Cited

U.S. PATENT DOCUMENTS

| | | | |
|---|---|---|---|
| 4,988,709 | 1/1991 | Ogata et al. | 514/314 |
| 5,106,854 | 4/1992 | Tsuji et al. | 514/312 |
| 5,395,944 | 3/1995 | Petersen et al. | 548/453 |
| 5,654,318 | 8/1997 | Takemura et al. | 514/314 |

FOREIGN PATENT DOCUMENTS

| | | |
|---|---|---|
| 2-56479 | 2/1990 | Japan . |
| 2-76875 | 3/1990 | Japan . |
| 5-25162 | 2/1993 | Japan . |
| 6-192262 | 7/1994 | Japan . |
| 6-239857 | 8/1994 | Japan . |

*Primary Examiner*—Evelyn Mei Huang
*Attorney, Agent, or Firm*—Wenderoth, Lind & Ponack, L.L.P.

[57] ABSTRACT

This invention relates to pyridonecarboxylic acid derivatives of the following general formula, esters thereof and salts thereof, as well as pharmaceutical preparations containing them.

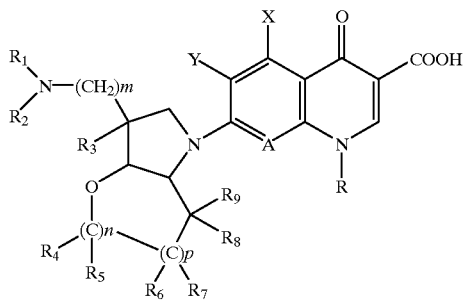

wherein:
R is cycloalkyl which may be substituted by halogen, or the like;
X is hydrogen, lower alkyl, amino or the like;
Y is hydrogen or halogen;
A is nitrogen or a group of the formula C—Z in which Z is lower alkoxy that may be substituted by halogen, or the like;
$R_1$ and $R_2$ may be the same or different and are each hydrogen or the like;
$R_3$ is hydrogen or lower alkyl;
$R_4$, $R_5$, $R_6$, $R_7$, $R_8$ and $R_9$ may be the same or different and are each hydrogen, halogen or lower alkyl;
m is 0 or 1; and
n and p may be the same or different and are each 0 or 1.

This invention also relates to bicyclic amine compounds useful as direct intermediates for the synthesis of the above-described pyridonecarboxylic acid derivatives.

15 Claims, No Drawings

PYRIDONECARBOXYLIC ACID DERIVATIVES AND INTERMEDIATES FOR THE SYNTHESIS THEREOF

This is national phase of PCT/JP97/00530, filed on Feb. 25, 1997 published as PCT 97/31919 on Sep. 4, 1997.

TECHNICAL FIELD

This invention relates to novel pyridonecarboxylic acid derivatives useful as antibacterial agents, and novel intermediates for the synthesis thereof.

BACKGROUND ART

A variety of antibacterial pyridonecarboxylic acid derivatives are known. For example, Japanese Patent Laid-Open No. 239857/'94 (corresponding to European Patent Application Laid-Open No. EP-A-603887) discloses compounds of the general formula (A)

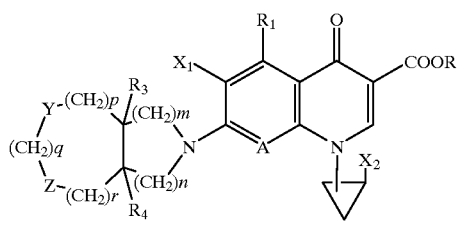

(A)

wherein:

$X_1$ and $X_2$ are each a halogen atom;

$R_1$ is an amino group which may have one or more substituents, or the like;

$R_3$ and $R_4$ are each a hydrogen atom, an alkyl group or the like;

Y is O, N, a methylene group or the like;

Z is O, S, a methylene group or the like;

m and n are each an integer of 0 to 2, the sum of them being 2 or 3;

p, q and r are each an integer of 0 to 3, the sum of them being 0 to 3;

A is N or C-X (in which X is a hydrogen atom, a halogen or the like); and

R is a hydrogen atom or the like.

In these compounds of the general formula (A), the bicyclic amino group constituting the substituent group at the 7-position is composed of a first ring containing a nitrogen atom and a second ring containing an oxygen atom or the like. However, as to the substituent group on the first ring, these compounds differ from the compounds of the present invention which are represented by the formula (I) that will be given later. Moreover, in the compounds of the above formula (A) which are specifically described in the aforementioned Japanese Patent Laid-Open No. 239857/'94, only the following three groups are disclosed as examples of the bicyclic amino groups at the 7-position.

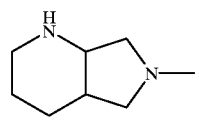

(a1)

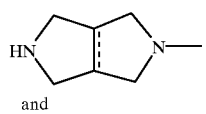

(a2)

and

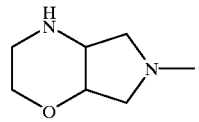

(a3)

Moreover, Japanese Patent Laid-Open No. 192262/'94 (corresponding to European Patent Application Laid-Open No. EP-A-589318) discloses compounds of the general formula (B)

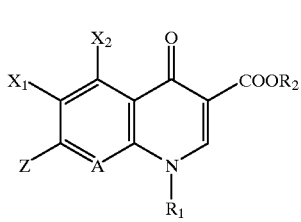

(B)

wherein:

$X_1$ is halogen or nitro;

$X_2$ is hydrogen, amino or the like;

$R_1$ is alkyl, cycloalkyl or the like;

$R_2$ is hydrogen or the like;

A is N or C-$R_5$ in which $R_5$ is hydrogen, halogen or the like; and

Z is a group of the formula

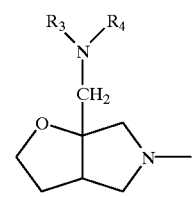

(b1)

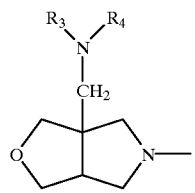

(b2)

-continued (b3)

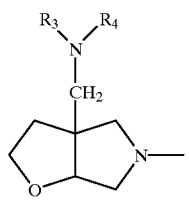

in which $R_3$ and $R_4$ are each hydrogen, methyl or the like. However, the bicyclic amino group (Z) constituting the substituent group at the 7-position in these compounds differs from that present in the compounds of the present invention, as to the mode of fusion between the first ring containing a nitrogen atom and the second ring containing an oxygen atom.

DISCLOSURE OF THE INVENTION

According to the present invention, there are provided novel pyridonecarboxylic acid derivatives of the following general formula (I) [which may hereinafter be referred to as the compounds (I) of the present invention], esters thereof and salts thereof.

(I)

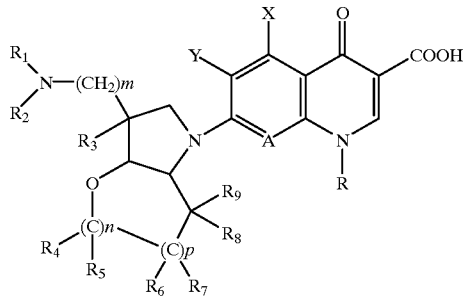

wherein:
R represents a lower alkyl group, a lower alkenyl group or a lower cycloalkyl group (all of which may optionally be substituted by one or more halogen atoms), or represents a phenyl group which may optionally be substituted by one or more halogen atoms and/or an amino group;

X represents a hydrogen atom, a halogen atom, a hydroxyl group, a lower alkyl group, a lower alkoxy group or an amino group which may be protected;

Y represents a hydrogen atom or a halogen atom;

A represents a nitrogen atom or a group of the formula C-Z in which Z represents a hydrogen atom, a halogen atom or a cyano group, represents a lower alkoxy group, a lower alkyl group, a lower alkylthio group, a lower alkenyl group or a lower alkynyl group (all of which may optionally be substituted by one or more halogen atoms), or combines with R to form a bridge represented by the formula —O—CH$_2$—CH(CH$_3$)—;

$R_1$ and $R_2$ may be the same or different and each represent a hydrogen atom, a lower alkyl group or an amino-protecting group;

$R_3$ represents a hydrogen atom or a lower alkyl group;

$R_4, R_5, R_6, R_7, R_8$ and $R_9$ may be the same or different and each represent a hydrogen atom, a halogen atom or a lower alkyl group;

m is 0 or 1; and
n and p may be the same or different and are each 0 or 1.

According to the present invention, there are also provided novel bicyclic amine compounds of the following general formula (II) and salts thereof which are useful as intermediates for the synthesis of pyridonecarboxylic acid derivatives of the above formula (I).

(II)

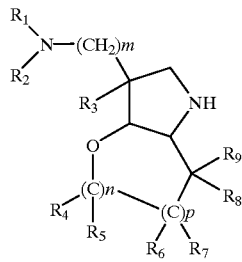

wherein $R_1, R_2, R_3, R_4, R_5, R_6, R_7, R_8, R_9$, m, n and p have the same meanings as described previously.

The compounds (I) of the present invention are structurally characterized by the fact that a conventionally unknown bicyclic amino group of the following general formula is joined to the 7-position of a specific pyridonecarboxylic acid or a position equivalent to the 7-position thereof.

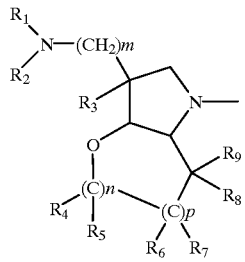

wherein $R_1, R_2, R_3, R_4, R_5, R_6, R_7, R_8, R_9$, m, n and p have the same meanings as described previously.

The compounds (I) of the present invention, which have the above-described structural features, exhibit excellent antibacterial activity, especially against Gram-positive bacteria, and are hence useful as antibacterial agents.

The compounds of the present invention will be more specifically explained hereinbelow.

As used herein, the term "halogen atom" comprehends, for example, fluorine, chlorine and bromine. The term "lower" means that the group modified by this word contains 1 to 7 carbon atoms, unless otherwise specified.

The term "lower alkyl" comprehends straight-chain and branched alkyl groups having 1 to 7 carbon atoms, and examples thereof include methyl, ethyl, propyl, isopropyl, butyl, tert-butyl and pentyl. The term "lower alkoxy" comprehends lower alkyloxy groups in which the lower alkyl portion has the above-described meaning, and examples thereof include methoxy, ethoxy, propoxy, isopropoxy and butoxy. The term "lower alkenyl" comprehends straight-chain and branched alkenyl groups having 2 to 7 carbon atoms, and examples thereof include vinyl, allyl, 1-propenyl and isopropenyl. The term "lower alkynyl" comprehends, for example, ethynyl and 1-propynyl. The term "lower cycloalkyl" comprehends cycloalkyl groups having 3 to 7 carbon atoms, and examples thereof include cyclopropyl, cyclobutyl, cyclopentyl and cyclohexyl. The term "lower alkylthio" comprehends, for example, methylthio and ethylthio.

The lower alkyl group, lower alkenyl group and lower cycloalkyl group which are used in the definition of R may optionally be substituted by one or more halogen atoms. Examples of the aforesaid groups substituted by one or more halogen atoms include fluoromethyl, difluoromethyl, trifluoromethyl, 2-fluoroethyl, 2-chloroethyl, 2,2-difluoroethyl, 2-fluorovinyl, 1-fluorovinyl, 2,2-difluorovinyl, 2-fluorocyclopropyl and 2-chlorocyclopropyl. On the other hand, the lower alkoxy group, lower alkyl group, lower alkylthio group, lower alkenyl group and lower alkynyl group which are used in the definition of Z may optionally be substituted by one or more halogen atoms. Examples of the aforesaid groups substituted by one or more halogen atoms include, in addition to the halogen-substituted lower alkyl and lower alkenyl groups which have been described above for R, fluoromethoxy, difluoromethoxy, trifluoromethoxy, difluoromethylthio, trifluoromethylthio, fluoroethynyl and trifluoropropynyl.

Examples of the phenyl group which may optionally be substituted by one or more halogen atoms and/or an amino group include 2,4-difluorophenyl, 3-amino-4,6-difluorophenyl, 4-chloro-2fluorophenyl, 2-chloro-4-fluorophenyl and 3-amino-4-fluorophenyl.

As the protecting group in the "amino-protecting group" or the "amino group which may be protected", there may be used any of various groups which can readily be eliminated by a common deprotection reaction such as hydrolysis or hydrogenolysis, without exerting no substantial influence on other structural parts.

Examples of amino-protecting groups which can readily be eliminated by hydrolysis (i.e., easily hydrolyzable amino-protecting groups) include oxycarbonyl groups such as ethoxycarbonyl, tert-butoxycarbonyl (which may be abbreviated as Boc), benzyloxycarbonyl, p-methoxybenzyloxycarbonyl, vinyloxycarbonyl and β-(p-toluenesulfonyl)ethoxycarbonyl; acyl groups such as formyl, acetyl and trifluoroacetyl; silyl groups such as trimethylsilyl and tert-butyldimethylsilyl; and tetrahydropyranyl, o-nitrophenylsulfenyl and diphenylphosphenyl.

Examples of amino-protecting groups which can readily be eliminated by hydrogenolysis (i.e., easily hydrogenolyzable amino-protecting groups) include arylsulfonyl groups such as p-toluenesulfonyl; phenyl- or benzyloxy-substituted methyl groups such as benzyl, trityl and benzyloxymethyl; arylmethoxycarbonyl groups such as benzyloxycarbonyl and o-methoxybenzyloxycarbonyl; and halogenoethoxycarbonyl groups such as β,β,β-trichloroethoxycarbonyl and β-iodoethoxycarbonyl.

As esters of the compounds (I) of the present invention, there may preferably be used esters which can be converted into the compounds (I) of the present invention by eliminating the alcohol group therefrom within or outside the living body by chemical or enzymological means.

The esters which can be converted into the corresponding free carboxylic acids by chemical means such as hydrolysis include, for example, lower alkyl esters such as methyl esters and ethyl esters. Moreover, the esters which can be converted into the corresponding free carboxylic acids not only by chemical means but also by enzymological means include, for example, lower alkanoyloxy-lower alkyl esters such as acetoxymethyl esters, 1-acetoxyethyl esters and pivaloyloxymethyl esters; lower alkoxycarbonyloxy-lower alkyl esters such as 1-ethoxycarbonyloxyethyl esters; aminoethyl esters such as 2-dimethylaminoethyl esters and 2-(1-piperidinyl)ethyl esters; and other esters such as 3-butyrolactonyl esters, choline esters, phthalidyl esters and (5-methyl-2-oxo-1,3-dioxol-4-yl) methyl esters.

As salts of the compounds (I) of the present invention, physiologically acceptable salts thereof are especially preferred. Examples thereof include salts formed with organic acids such as trifluoroacetic acid, acetic acid, lactic acid, succinic acid, methanesulfonic acid, maleic acid, malonic acid, gluconic acid and amino acids (e.g., aspartic acid and glutamic acid); salts formed with inorganic acids such as hydrochloric acid and phosphoric acid; metal salts such as sodium, potassium, zinc and silver salts; ammonium salts; and salts formed with organic bases such as trimethylamine, triethylamine and N-methylmorpholine.

Salts of the bicyclic amine compounds (II) of the present invention include acid addition salts formed with inorganic acids such as hydrochloric acid and sulfuric acid; and acid addition salts formed with organic acids such as formic acid, acetic acid, trifluoroacetic acid, methanesulfonic acid and p-toluenesulfonic acid.

The pyridonecarboxylic acid derivatives (I) and bicyclic amine compounds (II) of the present invention may sometimes exist in the form of hydrates and solvates. Moreover, these compounds of the present invention may exist in the form of optical isomers, stereoisomers (cis- and trans-forms) or mixtures thereof. These compounds are also within the scope of the present invention.

Preferred examples of the compounds (I) of the present invention are the compounds of the above general formula (I) in which n is 1. Among them, the following compounds of the above general formula (I) are more preferred.

(i) The compounds wherein R is a lower cycloalkyl group that may optionally be substituted by halogen, such as cyclopropyl or 2-fluorocyclopropyl, or a phenyl group that is substituted by one or more halogen atoms and/or an amino group, such as 2,4-difluorophenyl or 3-amino-4,6-difluorophenyl.

(ii) The compounds wherein X is a hydrogen atom, a lower alkyl group such as methyl, or an amino group.

(iii) The compounds wherein Y is a fluorine atom.

(iv) The compounds wherein A is a nitrogen atom or C-Z in which Z is a hydrogen atom; a halogen atom such as a fluorine or chlorine atom; a cyano group; a lower alkoxy group that may optionally be substituted by halogen, such as methoxy or difluoromethoxy; a lower alkyl group such as methyl; a lower alkylthio group such as methylthio; a lower alkenyl group such as vinyl; or a lower alkynyl group such as ethynyl.

(v) The compounds wherein $R_1$ and $R_2$ may be the same or different and are each a hydrogen atom or a lower alkyl group such as methyl.

(vi) The compounds wherein $R_3$ is a hydrogen atom.

(vii) The compounds wherein $R_4$, $R_5$, $R_6$, $R_7$, $R_8$ and $R_9$ may be the same or different and are each a hydrogen atom or a lower alkyl group such as methyl.

Still more preferred examples of the compounds of the present invention are the compounds of the above general formula (I) wherein R is a cyclopropyl, 2-fluorocyclopropyl, 2,4-difluorophenyl or 3-amino-4,6-difluorophenyl group; X is a hydrogen atom, a methyl group or an amino group; Y is a fluorine atom; A is a nitrogen atom or C-Z in which Z is a hydrogen atom, a fluorine atom, a chlorine atom, a methoxy group, a difluoromethoxy group, a methyl group, a methylthio group, a vinyl group, an ethynyl group or a cyano group; $R_1$ and $R_2$ may be the same or different and are each a hydrogen atom or a methyl group; $R_3$ is a hydrogen atom; $R_4$, $R_5$, $R_6$, $R_7$, $R_8$ and $R_9$ may be the same or different and are each a hydrogen atom or a methyl group; and n is 1. More specific examples thereof are the compounds described in the Examples which will be given later.

Excepting the compounds described in the Examples which will be given later, typical examples of the compounds (I) of the present invention are given below. Although the stereostructures thereof are not specified in the following designations, the compounds designated by the respective chemical names comprehend various isomers having different stereostructures.

7-(8-Amino-2-oxa-6-azabicyclo[3.3.0]oct-6-yl)-1-tert-butyl-6-fluoro-1,4-dihydro-4-oxo-1,8-naphthyridine-3-carboxylic acid.

7-(8-Amino-2-oxa-6-azabicyclo[3.3.0]oct-6-yl)-1-tert-butyl-6-fluoro-1,4-dihydro-8-methoxy-4-oxoquinoline-3-carboxylic acid.

7-(8-Amino-2-oxa-6-azabicyclo[3.3.0]oct-6-yl)-6,8-difluoro-1-(2-fluoroethyl)-1,4-dihydro-4-oxoquinoline-3-carboxylic acid.

7-(8-Amino-2-oxa-6-azabicyclo[3.3.0]oct-6-yl)-6-fluoro-1,4-dihydro-8-methoxy-4-oxo-1-vinylquinoline-3-carboxylic acid.

7-(4-Amino-6-oxa-2-azabicyclo[3.2.0]hept-2-yl)-1-cyclopropyl-6-fluoro-1,4-dihydro-8-methoxy-4-oxoquinoline-3-carboxylic acid.

7-(8-Amino-8-methyl-2-oxa-6-azabicylo[3.3.0]oct-6-yl)-1-cyclopropyl-6-fluoro-1,4-dihydro-8-methoxy-4-oxoquinoline-3-carboxylic acid.

7-(8-Amino-4-fluoro-2-oxa-6-azabicyclo[3.3.0]oct-6-yl)-1-cyclopropyl-6-fluoro-1,4-dihydro-8-methoxy-4-oxoquinoline-3-carboxylic acid.

7-(8-Amino-4,4-difluoro-2-oxa-6-azabicyclo[3.3.0]oct-6-yl)-1-cyclopropyl-6-fluoro-1,4-dihydro-8-methoxy-4-oxoquinoline-3-carboxylic acid.

7-(8-Amino-4-methyl-2-oxa-6-azabicyclo[3.3.0]oct-6-yl)-1-cyclopropyl-6-fluoro-1,4-dihydro-8-methoxy-4-oxoquinoline-3-carboxylic acid.

7-(8-Amino-2-oxa-6-azabicyclo[3.3.0]oct-6-yl)-1-cyclopropyl-6-fluoro-1,4-dihydro-8-methyl-4-oxoquinoline-3-carboxylic acid.

7-(8-Amino-2-oxa-6-azabicyclo[3.3.0]oct-6-yl)-1-cyclopropyl-6-fluoro-1,4-dihydro-5-hydroxy-8-methyl-4-oxoquinoline-3-carboxylic acid.

7-(8-Amino-2-oxa-6-azabicyclo[3.3.0]oct-6-yl)-1-cyclopropyl-6-fluoro-1,4-dihydro-5-hydroxy-8-methoxy-4-oxoquinoline-3-carboxylic acid.

1-(3-Amino-4,6-difluorophenyl)-7-(8-amino-2-oxa-6-azabicyclo[3.3.0]oct-6-yl)-8-chloro-6-fluoro-1,4-dihydro-4-oxoquinoline-3-carboxylic acid.

1-(3-Amino-4,6-difluorophenyl)-7-(8-amino-2-oxa-6-azabicyclo[3.3.0]oct-6-yl)-6-fluoro-1,4-dihydro-4-oxo-1,8-naphthyridine-3-carboxylic acid.

1-(3-Amino-4,6-difluorophenyl)-7-(8-amino-2-oxa-6-azabicyclo[3.3.0]oct-6-yl)-6-fluoro-1,4-dihydro-5-methyl-4-oxo-1,8-naphthyridine-3-carboxylic acid.

5-Amino-1-(3-amino-4,6-difluorophenyl)-7-(8-amino-2-oxa-6-azabicyclo[3.3.0]oct-6-yl)-6-fluoro-1,4-dihydro-4-oxo-1,8-naphthyridine-3-carboxylic acid.

7-(9-Amino-4,4-difluoro-2-oxa-7-azabicyclo[4.3.0]non-7-yl)-1-cyclopropyl-6-fluoro-1,4-dihydro-8-methoxy-4-oxoquinoline-3-carboxylic acid.

7-(8-Aminomethyl-2-oxa-6-azabicyclo[3.3.0]oct-6-yl)-1-cyclopropyl-6-fluoro-1,4-dihydro-8-methoxy-4-oxoquinoline-3-carboxylic acid.

Preferred examples of the bicyclic amine compounds (II) of the present invention are the compounds corresponding to the substituent groups located at the 7-position of the above-described pyridonecarboxylic acid derivatives.

The compounds (I) of the present invention may be prepared, for example, by an amination reaction or a ring closure reaction. A typical process based on the amination reaction is explained below.

The compounds (I) of the present invention, esters thereof and salts thereof may readily be prepared by reacting a compound of the general formula (III)

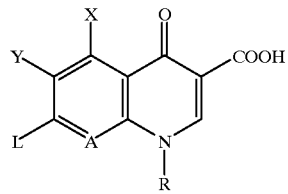

wherein L is a leaving group, R, X, Y and A have the same meanings as described previously, and the carboxyl and oxo groups present in the above formula may form a boron chelate bond therebetween, an ester thereof or a salt thereof with a bicyclic amine compound of the general formula (II)

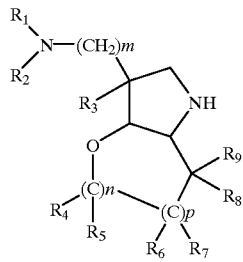

wherein $R_1$, $R_2$, $R_3$, $R_4$, $R_5$, $R_6$, $R_7$, $R_8$, $R_9$, m, n and p have the same meanings as described previously; and if a boron chelate part is present in the product, hydrolyzing it.

Examples of the leaving group L in the general formula (III) include halogen atoms, lower alkoxy groups, lower alkylthio groups, lower alkylsulfonyl groups, lower alkylsulfinyl groups, lower alkylsulfonyloxy groups and arylsulfonyloxy groups. Among them, halogen atoms such as fluorine and chlorine are preferred.

The reaction of the compound (II) with the compound (III) may usually be carried out by stirring a mixture thereof in an inert solvent at a temperature of about 10 to 180° C. and preferably about 20 to 130° C., for a period of time ranging from about 10 minutes to 7 days and preferably from about 30 minutes to 3 days. The inert solvents which can be used for this purpose include, for example, water, methanol, ethanol, acetonitrile, chloroform, pyridine, N,N-dimethylformamide, dimethyl sulfoxide and 1-methyl-2-pyrrolidone. These solvents may be used alone or in admixture.

This reaction is generally carried out in the presence of an acid acceptor by using the compound (II) in an amount equivalent to or in slightly excess of that of the compound (III). However, the compound (II) may be used in excess so as to function additionally as an acid acceptor. Examples of the acid acceptor include organic bases such as 1,8-diazabicyclo[5.4.0]-7-undecene (DBU), triethylamine, pyridine, quinoline and picoline; and inorganic bases such as sodium hydroxide, potassium hydroxide, sodium carbonate, potassium carbonate, sodium hydrogen carbonate and potassium hydrogen carbonate. These acid acceptor may usually be used in an amount of about 1 to 3 moles per mole of the compound (II).

Compounds (III) are well known or may be prepared according to well-known processes. Bicyclic amine compounds (II) are all novel and the processes for the preparation thereof will be described later.

When the compound (I) of the present invention which has been prepared by the above-described amination reaction has an amino-protecting group and/or the compound (I) of the present invention is obtained in the form of an ester, the amino-protecting group and/or ester may optionally be eliminated or converted. If a free acid is obtained thereby, it may be converted into a salt as required, or if a salt is obtained, it may be converted into a free acid as required. The conversion of an ester into a free acid may be carried out by a hydrolysis reaction. The elimination of an amino-protecting group may be carried out by subjecting the resulting compound (I) to a hydrolysis reaction or a hydrogenolysis reaction according to the type of the protecting group. Thus, there can be obtained a compound (I) of the present invention in which the amino-protecting group has been converted into a hydrogen atom. The hydrolysis reaction and hydrogenolysis reaction are described below.

The hydrolysis reaction may be carried out by bringing an ester of a compound (I) of the present invention and/or a compound (I) of the present invention having an easily hydrolyzable amino-protecting group into contact with water in a suitable solvent. In order to accelerate this reaction, it is usually carried out in the presence of an acid or a base. Usable acids include inorganic acids such as hydrochloric acid, hydrobromic acid, sulfuric acid and phosphoric acid; and organic acids such as acetic acid, trifluoroacetic acid, formic acid and p-toluenesulfonic acid. Usable bases include metal hydroxides such as sodium hydroxide and barium hydroxide; carbonates such as sodium carbonate and potassium carbonate; and sodium acetate.

Usually, water is used as the solvent. However, according to the properties of the aforesaid compound(s), a water-miscible organic solvent such as ethanol, ethylene glycol dimethyl ether or dioxane may be used in combination with water. The reaction temperature may usually range from about 0 to 150° C. and preferably from about 30 to 100° C.

This reaction may also be carried out by heating the aforesaid compound(s) directly in the presence of an acid as described above, and then adding water thereto.

The elimination of an amino-protecting group by hydrogenolysis may advantageously be carried out by treating a compound (1) of the present invention having an easily hydrogenolyzable amino-protecting group with hydrogen gas in a solvent in the presence of a catalyst. The catalysts which can be used in this reaction include, for example, catalysts for hydrogenation, such as platinum, palladium and Raney nickel catalyst. Usable solvents include, for example, ethylene glycol, dioxane, N,N-dimethylformamide, ethanol, acetic acid and water. This reaction may be carried out at a temperature of about 60° C. or below and is usually carried out at room temperature.

When the easily hydrogenolyzable amino-protecting group is benzyl, trityl, benzyloxycarbonyl, p-toluenesulfonyl or the like, the protecting group may also be eliminated by metallic sodium treatment in liquid ammonia at a temperature of about −50 to −20° C.

The compounds (I) of the present invention, which have been prepared by the above-described amination reaction, may be isolated and purified according to any conventional procedure. These compounds are obtained in the form of salts, free acids or hydrates, depending on the conditions of isolation and purification. However, according to the intended purposes, these forms may be changed into each other to obtain the compounds of the present invention in desired forms.

The stereoisomers of the compounds (I) of the present invention may be separated from each other by any conventional method such as fractional crystallization or chromatography. Moreover, their optical isomers may be isolated by the application of a known optical resolution method.

The compounds (I) of the present invention and salts thereof, which can be obtained in the above-described manner, are all novel compounds and are valuable as antibacterial agents because of their high antibacterial activities. The compounds (I) of the present invention and salts thereof can be used not only as drugs for human beings and other animals, but also as agricultural chemicals, food preservatives and the like.

Esters of the compounds (I) of the present invention are valuable as starting materials for the synthesis of the compounds (I) of the present invention. However, if these esters themselves are readily converted into the compounds (I) of the present invention within the living body, they are useful as prodrugs. Accordingly, they may be used as antibacterial agents similarly to the compounds (I) of the present invention.

The compounds (II) used as starting materials in the above-described amination reaction process may be prepared, for example, by eliminating the amino-protecting group $R_{10}$ from a compound of the general formula (IV)

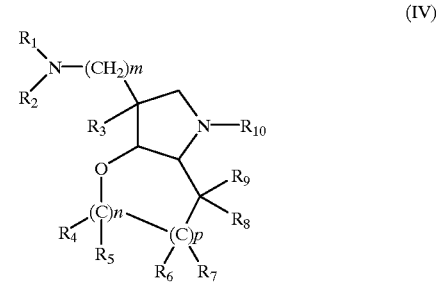

(IV)

wherein $R_{10}$ is an amino-protecting group, and $R_1$, $R_2$, $R_3$, $R_4$, $R_5$, $R_6$, $R_7$, $R_8$, $R_9$, m, n and p have the same meanings as described previously, and thereby converting it into a hydrogen atom.

In this case, examples of the amino-protecting group $R_{10}$ include the above-described easily hydrogenolyzable amino-protecting groups and easily hydrolyzable amino-protecting groups.

When $R_1$ and/or $R_2$ in the compound (IV) are amino-protecting groups, it is desirable for subsequent reactions to employ, for $R_{10}$, an amino-protecting group differing in character from the amino-protecting groups represented by $R_1$ and/or $R_2$. For example, when the amino-protecting groups represented by $R_1$ and/or $R_2$ are easily hydrolyzable amino-protecting groups such as tert-butoxycarbonyl, an easily hydrogenolyzable amino-protecting group such as benzyl or trityl is preferably chosen for $R_{10}$.

The elimination reaction for the amino-protecting group $R_{10}$ may be carried out by subjecting the compound (IV) to a hydrogenolysis or hydrolysis reaction which has previously been explained.

When $R_1$ and/or $R_2$ in the compound obtained as a result of this elimination reaction are amino-protecting groups, they may optionally be eliminated and converted into hydrogen atoms in the same manner. If a free base is obtained thereby, it may be converted into a salt in the usual manner as required, or if a salt is obtained, it may be converted into a free base as required.

The stereoisomers of the compounds (II) of the present invention which are prepared in the above-described manner may be separated from each other by any conventional method such as fractional crystallization or chromatography. Moreover, their optical isomers may be isolated by the application of a known optical resolution method.

The compounds (IV) are also novel, and they may be prepared according to the processes shown in the following reaction schemes 1–9 or processes equivalent thereto.

Reaction scheme 1

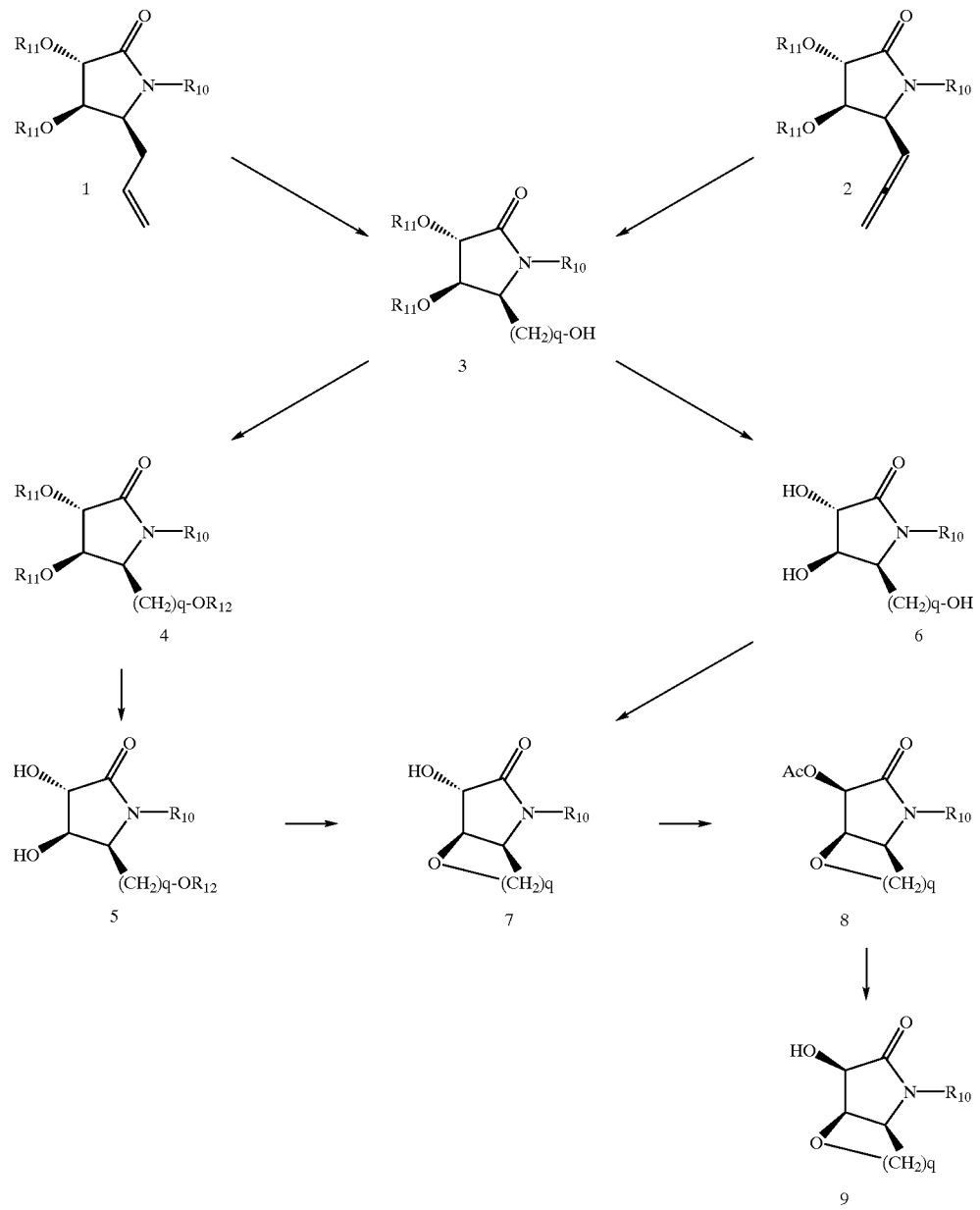

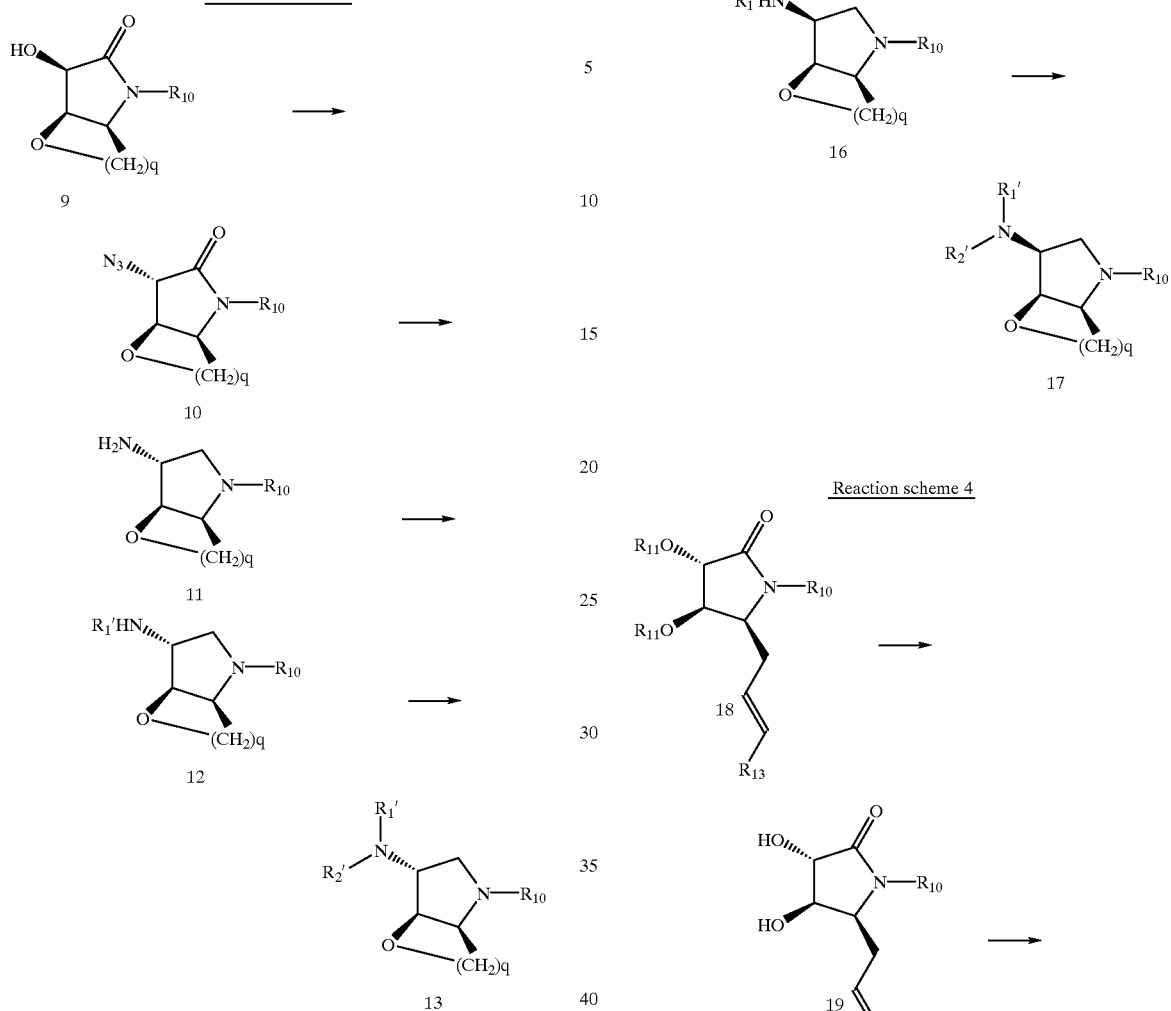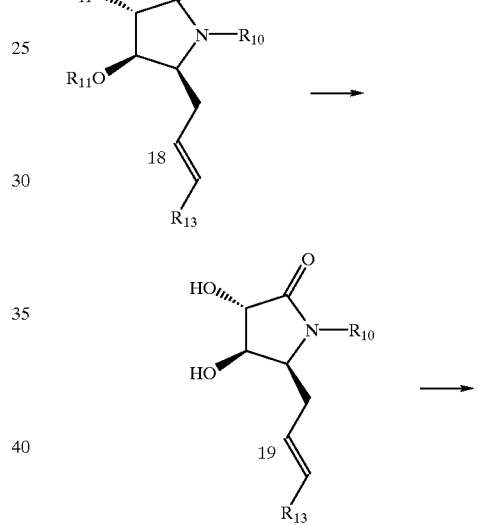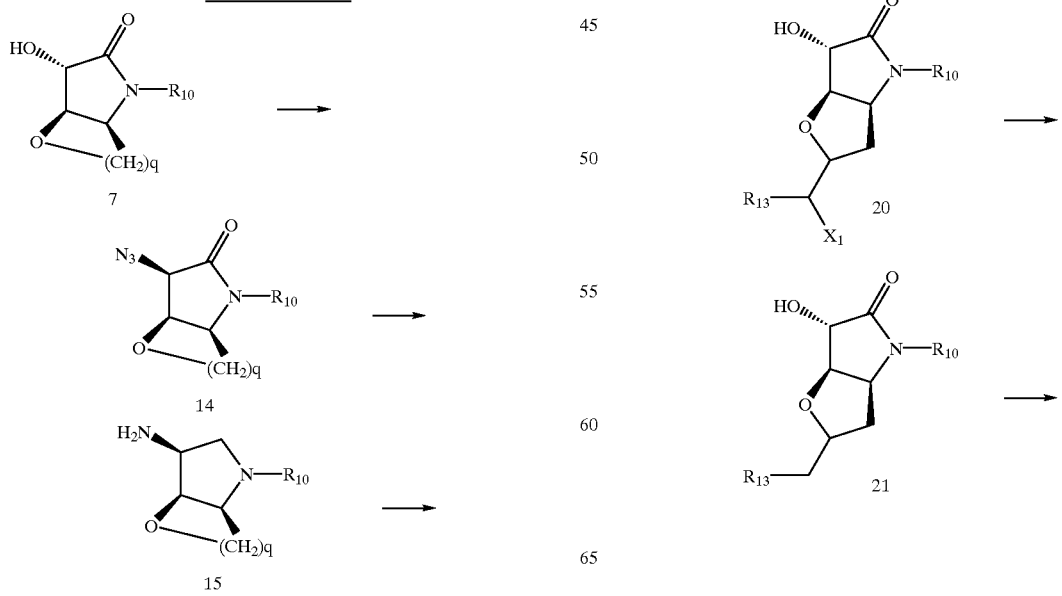

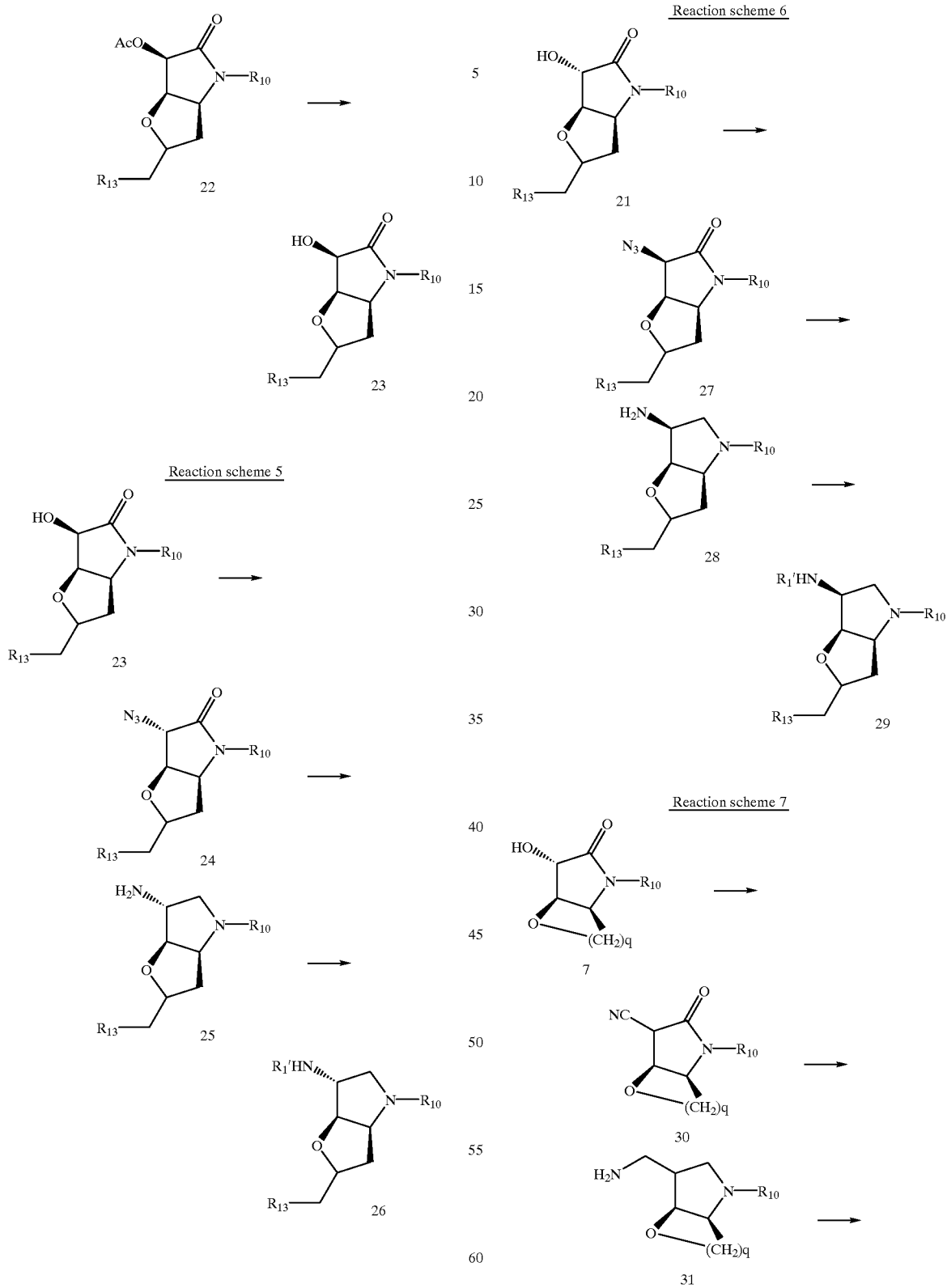

17
-continued
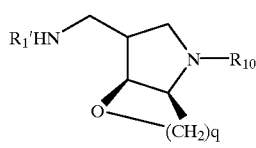
5
Reaction scheme 8
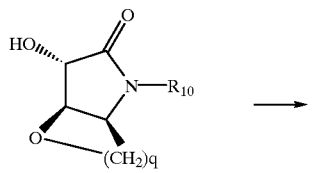
7
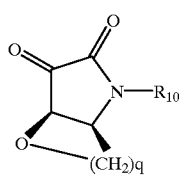
33
18
-continued
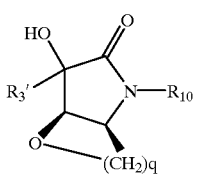 
34
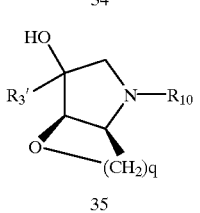 
35
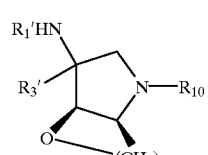
36
Reaction scheme 9
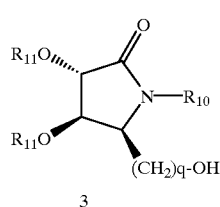  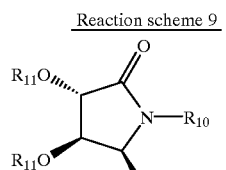
3 → 37
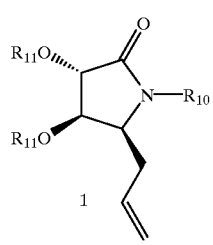  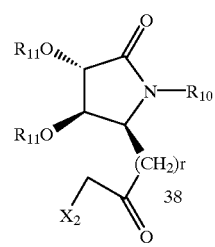  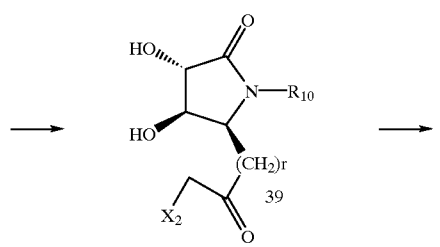
1 → 38 → 39 →
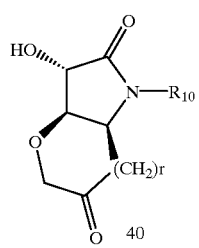  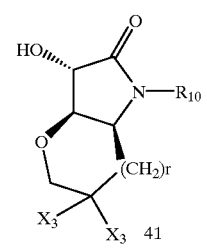  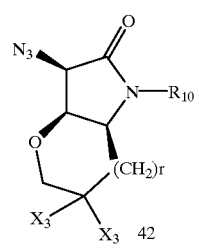 
40 → 41 → 42 →

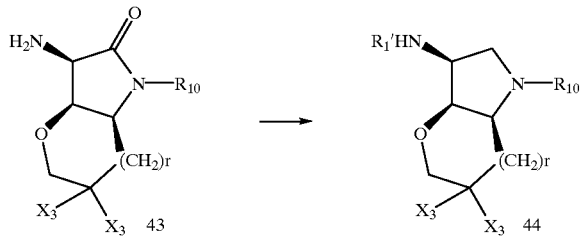

wherein:

$R_{10}$ has the same meaning as described previously;

$R_{11}$ represents an alcohol-protecting group such as tert-butyidimethylsilyl, acetyl or tetrahydroyranyl;

$R_{12}$ represents a (lower alkyl)sulfonyl, a (halogeno lower alkyl)sulfonyl group or an arylsulfonyl group;

$R_{13}$ represents a hydrogen atom or a lower alkyl group;

$R_1'$ represents an amino-protecting group;

$R_2'$ and $R_3'$ each represent a lower alkyl group;

$X_1$, $X_2$ and $X_3$ each represent a halogen atom;

q represents an integer of 1 to 3; and r is 0 or 1.

Now, the foregoing reaction schemes will be briefly explained herein below.

Reaction Scheme 1

A compound 3 (q=1 or 2) is obtained by oxidizing a known compound 1 or 2 with ozone and then reducing the resulting product. Moreover, the compound 3 (q=3) may be obtained by the hydroboration of the compound 1. The terminal alcohol group of the compound 3 is sulfonylated to yield a compound 4, the alcohol-protecting groups $R_{11}$ thereof are eliminated to yield a compound 5, and this is converted into a compound 7 by ring closure. Alternatively, the compound 7 may also be obtained by eliminating the alcohol-protecting groups $R_{11}$ of the compound 3 to yield a compound 6, and reacting this compound 6 with a sulfonylation reagent in the presence of a base. Subsequently, the hydroxyl group of the compound 7 is inverted via a compound 8 to yield a compound 9.

Reaction Scheme 2

The hydroxyl group of the compound 9 obtained in the above-described manner is sulfonylated and then substituted by an azide to yield a compound 10, and this is reduced to yield a compound 11. Thereafter, a desired compound 12 falling under the category of the compounds (IV) may be obtained by protecting the amino group of the compound 11. Furthermore, a desired compound 13 falling under the category of the compounds (IV) may be obtained by alkylating the compound 12 or by reducing the amino-protecting group $R_1'$ to form a lower alkyl group $R_2'$ and then introducing an amino-protecting group $R_1'$.

Reaction Scheme 3

Desired compounds 16 and 17 falling under the category of the compounds (IV) may be obtained from the compound 7 in exactly the same manner as in the reaction scheme 2.

Reaction Scheme 4

The alcohol-protecting group $R_{11}$ of a compound 18 is eliminated to yield a compound 19, and this is treated with a halogenation reagent to yield a compound 20. The compound 20 is dehalogenated to yield a compound 21, and the hydroxyl group of the compound 21 is inverted via a compound 22 to yield a compound 23.

Reaction Scheme 5

A desired compound 26 falling under the category of the compounds (IV) may be obtained from the compound 23 in exactly the same manner as in the reaction scheme 2.

Reaction Scheme 6

A desired compound 29 falling under the category of the compounds (IV) may be obtained from the compound 21 in exactly the same manner as in the reaction scheme 2.

Reaction Scheme 7

The hydroxyl group of the compound 7 obtained in the reaction scheme 1 is sulfonylated and then substituted by a cyanide to yield a compound 30, and this is reduced to yield a compound 31. Thereafter, a desired compound 32 falling under the category of the compounds (IV) may be obtained by protecting the amino group of the compound 31.

Reaction Scheme 8

The compound 7 obtained in the reaction scheme 1 is oxidized to yield a compound 33, and this is reacted with a lower alkyl metal reagent to yield a compound 34. The compound 34 is reduced to a compound 35. Thereafter, a desired compound 36 falling under the category of the compounds (IV) may be obtained by the Ritter reaction.

Reaction Scheme 9

The compound 3 (q=2) obtained in the reaction scheme 1 is dehydrated to yield a compound 37, and this compound 37 is oxidized and halogenated to yield a compound 38 (r=0). A compound 38 (r=1) may be obtained by oxidizing and halogenating the compound 1. The alcohol-protecting group $R_{11}$ of the compound 38 is eliminated to yield a compound 39, and this is converted into a compound 40 by ring closure. The compound 40 is halogenated to yield a compound 41. Thereafter, a desired compound 44 falling under the category of the compounds (IV) may be obtained from the compound 41 in exactly the same manner as in the reaction scheme 2.

The foregoing various reactions are more specifically described in Examples A to M which will be given later.

Now, the in vitro antibacterial activities and in vivo effects of various compounds (I) in accordance with the present invention are described with reference to the following experimental data.

Table 1 shows their minimum inhibitory concentrations (MIC; $\mu$g/ml) as measured according to the procedure described in Chemotherapy, 29(1), 76 (1981), and Table 2 shows their effects ($ED_{50}$; mg/kg) on systemic infection in mice. The effects ($ED_{50}$; mg/kg) on systemic infection in mice were determined as follows: Male Std-ddy strain mice (weighing about 20 g) were infected with each of the pathogenic bacteria shown in Table 2 by administering $5 \times 10^3$ viable cells intraperitoneally to each mouse. Then, a suspension of each test compound in 0.4% carboxymethylcellulose was orally administered twice, i.e., immediately after infection and 6 hours after infection. Seven days after infection, the $ED_{50}$ value was calculated from the survival rate of each mouse group by probit analysis.

As a reference compound, there was used enoxacin [1-ethyl-6-fluoro-1,4-dihydro-4-oxo-7-(1-piperazinyl-1,8-naphthyridine-3-carboxylic acid; hereinafter abbreviated as ENX] that is an excellent antibacterial agent currently on the market.

The test compounds shown in the following Tables 1 and 2 are identified by the respective numbers of the Examples which will be given later.

TABLE 1

In vitro antibacterial activities (MIC: µg/ml)

| | Strain | | | |
|---|---|---|---|---|
| | *Staphylococcus aureus* | | *Escherichia coli* | *Pseudomonas aeruginosa* |
| Example | 50774 | MS16405 | NIHJ JC-2 | No 12 |
| 1 | ≦0.003 | 0.39 | 0.013 | 0.39 |
| 2 | 0.006 | 0.39 | 0.013 | 0.39 |
| 3 | 0.013 | 1.56 | 0.006 | 0.2 |
| 4 | 0.006 | 0.39 | 0.025 | 0.78 |
| 5 | ≦0.003 | 0.39 | 0.025 | 0.78 |
| 6 | 0.025 | 1.56 | 0.025 | 1.56 |
| 7 | 0.006 | 0.39 | 0.025 | 0.39 |
| 8 | 0.013 | 3.13 | 0.2 | 1.56 |
| 9 | 0.025 | 1.56 | 0.05 | 1.56 |
| 10 | 0.013 | 0.39 | 0.1 | 3.13 |
| 11 | 0.013 | — | 0.25 | 0.39 |
| 12 | 0.013 | 0.39 | 0.1 | 1.56 |
| 13 | 0.013 | 1.56 | 0.05 | 0.78 |
| 14 | 0.025 | 1.56 | 0.025 | 1.56 |
| 15 | 0.025 | 0.78 | 0.013 | 0.78 |
| 16 | 0.006 | 1.56 | 0.1 | 1.56 |
| 17 | 0.05 | — | 0.1 | 0.78 |
| 18 | 0.025 | 1.56 | 0.006 | 0.39 |
| ENX | 0.39 | 100 | 0.05 | 0.78 |
| 19 | 0.013 | 0.78 | 0.1 | 1.56 |
| 20 | 0.1 | 3.13 | 0.05 | 1.56 |
| 21 | ≦0.003 | 0.78 | 0.013 | 0.39 |
| 22 | 0.05 | — | ≦0.003 | 0.39 |
| 23 | ≦0.003 | 0.78 | 0.025 | 0.78 |
| 24 | 0.013 | 1.56 | 0.025 | 0.78 |
| 25 | 0.025 | 1.56 | 0.025 | 1.56 |
| 26 | 0.05 | — | 0.013 | 0.39 |
| 27 | 0.025 | 1.56 | 0.025 | 1.56 |
| 28 | 0.025 | 0.78 | 0.025 | 1.56 |
| 29 | 0.025 | — | 0.025 | 0.39 |
| 30 | 0.013 | 3.13 | 0.05 | 0.78 |
| 31 | 0.013 | 0.78 | 0.1 | 0.78 |
| 32 | 0.013 | 0.78 | 0.1 | 1.56 |
| 33 | 0.025 | 1.56 | 0.05 | 3.13 |
| 34 | 0.05 | 6.25 | 0.05 | 1.56 |
| 35 | 0.025 | 6.25 | 0.1 | 3.13 |
| 56 | 0.013 | 0.78 | 0.2 | 3.13 |
| ENX | 0.39 | 100 | 0.05 | 0.78 |
| 37 | 0.05 | 6.25 | 0.1 | 3.13 |
| 38 | 0.1 | — | 0.05 | 3.13 |
| 39 | 0.025 | 3.13 | 0.2 | 0.78 |
| 40 | 0.025 | 1.56 | 0.1 | 3.13 |
| ENX | 0.39 | 100 | 0.05 | 0.78 |

TABLE 2

Effects (ED$_{50}$; mg/kg) on systemic infection in mice

| | Strain |
|---|---|
| Example | *Staphylococcus aureus* 50774 |
| 1 | 0.36 |
| 2 | 0.383 |
| 3 | 0.398 |
| 4 | 0.246 |
| 5 | 0.257 |

TABLE 2-continued

Effects (ED$_{50}$; mg/kg) on systemic infection in mice

| | Strain |
|---|---|
| Example | *Staphylococcus aureus* 50774 |
| 6 | 0.292 |
| 7 | 0.331 |
| 8 | 0.345 |
| 9 | 0.415 |
| 10 | 0.465 |
| 11 | 0.579 |
| 12 | 0.715 |
| 13 | 0.778 |
| 14 | ≦0.78 |
| 15 | 1.12 |
| 16 | 0.78 |
| 17 | 0.78 |
| 18 | 0.928 |
| 19 | 0.928 |
| ENX | 9.89 |

As shown in Tables 1 and 2, the compounds (I) of the present invention exhibit an excellent in vitro antibacterial activity and in vivo effect. In particular, with respect to antibacterial activity against Gram-positive bacteria, the compounds (I) of the present invention are much more powerful than ENX (enoxacin).

Thus, the compounds (I) of the present invention, esters thereof, and physiologically acceptable salts thereof can suitably be used as antibacterial agents for the treatment of bacterial diseases in human beings and other animals.

When the compounds (I) of the present invention are used as antibacterial agents in human beings, their dosage may vary according to the age and body weight of the patient, the severity of symptoms, the route of administration, and the like. However, it is recommended to administer them in a daily dose of 5 mg to 5 g which may be given once or in several divided doses. Although the route of administration may be oral, parenteral or topical, oral administration is recommended.

The compounds (I) of the present invention, may be directly administered in their bulk form to human beings and other animals. However, they are usually combined with one or more pharmaceutically acceptable additives and administered in the form of pharmaceutical preparations (or pharmaceutical compositions). Such pharmaceutical preparations include tablets, solutions, capsules, granules, fine subtilaes, powders, syrups, injections, suppositories, ointments, sprays, ophthalmic solutions and the like. These pharmaceutical preparations may be made in the usual manner by using common additives. For example, as additives for oral preparations, there may be used various solid and liquid carriers or diluents which are commonly used in the field of pharmaceutics and do not react with the compounds (I) of the present invention, such as starch, mannitol, crystalline cellulose, carboxymethylcellulose calcium, water and ethanol. Moreover, as additives for injections, there may be used various additives which are commonly used in the field of injections, such as water, physiological saline, glucose solutions and transfusions.

The aforesaid sprays and ointments may also be used for purposes of therapy and treatment in the fields of otorhinolaryngology and ophthalmology.

EXAMPLES

The present invention is further illustrated by the following examples. Examples A to M relate to the preparation of bicyclic amine compounds (II) useful as intermediates, Examples 1 to 48 relate to the preparation of compounds (I) in accordance with the present invention, and Example N relates to a pharmaceutical preparation.

The asterisks (*) in "R*" and "S*" found in the names of compounds indicate that the stereostructures of such compounds are not absolute but relative. Moreover, the stereostructures of the chemical structural formulae given below are not absolute but relative.

The abbreviations used in the examples have the following meanings.

| Boc: | tert-butoxycarbonyl |
|---|---|
| Me: | methyl |
| 2,4-F$_2$Ph: | 2,4-difluorophenyl |

Example A (−)-(1R*,5S*,8R*)-8-(tert-butoxycarbonylamino)-2-oxa-6-azabicyclo[3.3.0]octane [a compound (II) in which R$_1$=Boc; R$_2$, R$_3$, R$_4$, R$_5$, R$_8$, R$_9$=H; m=0; n=1; and p=0].

Step 1

1,200 ml of a 60% aqueous solution of acetic acid was added to 125.5 g of (3R*,4S*,5R*)-1-benzyl-3,4-bis(tert-butyldimethylsilyloxy)-5-(2-hydroxyethyl)-2-pyrrolidinone which had been prepared according to the procedure described in J. Org. Chem. 60, 103–108 (1995) by using D-tartaric acid as the starting material. After this mixture was refluxed overnight and concentrated under reduced pressure, 300 ml of concentrated aqueous ammonia and 500 ml of methanol were added to the resulting residue, followed by stirring at room temperature overnight. After the reaction mixture was concentrated under reduced pressure, the resulting residue was purified by silica gel column chromatography (using a 10:1 mixture of chloroform and methanol as the eluent) to obtain 35 g of (3R*,4S*,5R*)-1-benzyl-3,4-dihydroxy-5-(2-hydroxyethyl)-2-pyrrolidinone.

IR (neat), cm$^{-1}$: 3370, 1682.

MS (m/z): 252 (MH$^+$).

$^1$H-NMR (CDCl$_3$), δ: 7.10–7.32 (m, 5H), 5.52 (br s, 2H), 4.90 (d, 1H, J=15.0 Hz), 4.50 (d, 1H, J=7.5 Hz), 4.21 (br t, 1H, J=7.5 Hz), 3.94 (d, 1H, J=15.0 Hz), 3.55 (br s, 3H), 2.20–2.00 (br s, 1H), 1.86 (br s, 2H).

Step 2

35 g of the compound obtained in the preceding step 1 was added to 400 ml of pyridine, and cooled with ice. Then, 26.6 g of p-toluenesulfonyl chloride was added thereto, followed by stirring overnight. Thereafter, water and chloroform were added to the reaction mixture so as to extract the product in an organic layer. This organic layer was washed with a 10% aqueous solution of hydrochloric acid and then dried over anhydrous magnesium sulfate. The solvent was distilled off under reduced pressure to obtain 24 g of (1R*,5S*,8S*)-6-benzyl-8-hydroxy-7-oxo-2-oxa-6-azabicyclo[3.3.0]octane in the form of an oil.

IR (neat), cm$^{-1}$: 3390, 1692.

MS (m/z): 234 (MH$^+$).

$^1$H-NMR (CDCl$_3$), δ: 7.40–7.18 (m, 5H), 4.84 (d, 1H, J=15.0 Hz), 4.49 (br, 1H), 4.42 (dd, 1H, J=6.5, 1.7 Hz), 4.32 (br, 1H), 4.16–4.06 (m, 2H), 3.92–3.66 (m, 2H), 1.92–1.82 (m, 2H).

Step 3

(1) 14 g of the compound obtained in the preceding step 2 was added to 250 ml of methylene chloride, and cooled with ice. Then, 14.6 ml of pyridine was added thereto, and 13.1 ml of trifluoromethanesulfonic acid anhydride was slowly added thereto. After 2 hours, 550 ml of dimethylformamide and 58.9 g of potassium acetate were added to the reaction mixture, followed by stirring overnight. After insoluble matter was filtered off, the reaction mixture was concentrated under reduced pressure. Then, water and chloroform were added to the resulting residue so as to extract the product in an organic layer. Thereafter, the solvent was distilled off under reduced pressure to obtain crude (1R*,5S*,8R*)-8-acetoxy-6-benzyl-7-oxo-2-oxa-6-azabicyclo[3.3.0]octane.

(2) Subsequently, 500 ml of ethanol and 200 ml of concentrated aqueous ammonia were added to this compound, followed by stirring at room temperature overnight. The reaction mixture was concentrated under reduced pressure, and water and chloroform were added to the resulting residue so as to extract the product in an organic layer. Thereafter, the solvent was distilled off under reduced pressure, and the resulting residue was purified by silica gel column chromatography (using a 30:1 mixture of chloroform and methanol as the eluent) to obtain 9.2 g of (1R*,5S*,8R*)-6-benzyl-8-hydroxy-7-oxo-2-oxa-6-azabicyclo[3.3.0]octane.

IR (neat), cm$^{-1}$: 3381, 1694.

MS (m/z): 234 (MH$^+$).

$^1$H-NMR (CDCl$_3$), δ: 7.40–7.20 (m, 5H), 4.93 (d, 1H, J=15.0 Hz), 4.50 (dd, 1H, J=6.0, 5.0 Hz), 4.28 (d, 1H, J=6.0 Hz), 4.09 (d, 1H, J=15.0 Hz), 4.08–3.93 (m, 2H), 3.80–3.66 (m, 1H), 3.22 (br s, 1H), 2.24–2.11 (m, 1H), 2.01–1.81 (m, 1H).

Step 4

9.2 g of the compound obtained in the preceding step 3(2) was added to 100 ml of methylene chloride, and cooled with ice. Then, 9.5 ml of pyridine was added thereto, and 9.1 ml of trifluoromethanesulfonic acid anhydride was slowly added thereto. After 2 hours, 300 ml of dimethylformamide and 24.4 g of sodium azide were added to the reaction mixture, followed by stirring overnight.. The reaction mixture was concentrated under reduced pressure, and water and chloroform were added to the resulting residue so as to extract the product in an organic layer. After this organic layer was washed with a dilute aqueous solution of hydrochloric acid and then dried over anhydrous magnesium sulfate, the solvent was distilled off under reduced pressure to obtain 7.4 g of (1R*,5S*,8S*)-8-azido-6-benzyl-7-oxo-2-oxa-6-azabicyclo[3.3.0]octane.

IR (neat), cm$^{-1}$: 2109, 1694.

$^1$H-NMR (CDCl$_3$), δ: 7.40–7.20 (m, 5H), 4.93 (d, 1H, J=15.0 Hz), 4.23 (dd, 1H, J=6.0, 1.5 Hz), 4.16–4.02 (m, 3H), 3.94–3.82 (m, 1H), 3.81–3.67 (m, 1H), 2.00–1.80 (m, 2H).

Step 5

(1) 7.4 g of the compound obtained in the preceding step 4 was added to 300 ml of tetrahydrofuran, and cooled with ice. Then, 116 ml of a 1.0M solution of borane-tetrahydrofuran complex in tetrahydrofuran was added thereto. This mixture was heated after 30 minutes and refluxed overnight. The reaction mixture was cooled to room temperature and freed of excess borane by treatment with ethanol. After the reaction mixture was concentrated under reduced pressure, 600 ml of ethanol as added to the resulting residue, followed by refluxing overnight. After the reaction mixture was concentrated under reduced pressure, a 10% aqueous solution of hydrochloric acid was added to the resulting residue so as to extract the product in an aqueous layer. This aqueous layer was washed with chloroform, alkalified with a 20% aqueous solution of sodium hydroxide, and then extracted with chloroform. After the extract was dried over anhydrous magnesium sulfate, the solvent was distilled off under reduced pressure to obtain 5.5 g of (1R*,5R*,8S*)-8-amino-6-benzyl-2-oxa-6-azabicyclo[3.3.0]octane.

(2) Subsequently, this compound was added to 100 ml of methanol, and cooled with ice. Then, 7.2 g of di-tert-butyl dicarbonate was added thereto, followed by stirring overnight. After the reaction mixture was concentrated under reduced pressure, the resulting residue was subjected to silica gel column chromatography (using a 6:1 mixture of n-hexane and ethyl acetate as the eluent). Thus, there was obtained 7.0 g of (1R*,5R*,8S*)-6-benzyl-8-(tert-butoxycarbonylamino)-2-oxa-6-azabicyclo[3.3.0]octane.

Melting point: 115–116° C. (recrystallized from ethyl acetate).

$[\alpha]_D^{27}$=+2.3° (c=1.02, methanol).

Step 6

5.4 g of the compound obtained in the preceding step 5(2) was dissolved in 100 ml of ethanol, and 350 mg of 5% palladium-carbon was added thereto. Then, this mixture was made to absorb a stoichiometric amount of hydrogen at 40° C. After the catalyst was removed by filtration, the solvent was distilled off under reduced pressure. The resulting crude crystals were recrystallized from ethyl ether-diisopropyl ether to obtain 3.5 g of the desired (−)-(1R*,5S*,8R*)-8-(tert-butoxycarbonylamino)-2-oxa-6-azabicyclo[3.3.0]octane.

Melting point: 110–111° C.

IR (KBr), cm$^{-1}$: 3377, 3228, 1680.

$[\alpha]_D^{29}$=−44.4° (c=1.03, methanol).

$^1$H-NMR (CDCl$_3$), δ: 4.22 (d, 1H, J=5.5 Hz), 4.02–3.69 (m, 4H), 3.15 (dd, 1H, J=11.5, 5.0 Hz), 2.84 (dd, 1H, J=11.5, 3.0 Hz), 2.19–1.99 (m, 1H), 1.83–1.68 (m, 2H), 1.45 (s, 9H).

Example B (−)-(1R*,5S*,8S*)-8-(tert-butoxycarbonylamino)-2-oxa-6-azabicyclo[3.3.0]octane [a compound (II) in which R$_1$=Boc; R$_2$, R$_3$, R$_4$, R$_5$, R$_8$, R$_9$=H; m=0; n=1; and p=0].

The (1R*,5S*,8S*)-6-benzyl-8-hydroxy-7-oxo-2-oxa-6-azabicyclo[3.3.0]octane obtained in the step 2 of Example A was treated in the same manner as described in the steps 4 to 6 of Example A. Thus, the desired title compound was obtained.

$[\alpha]_D^{27}$=−79.3° (c=1.02, methanol).

MS (m/z): 229 (MH$^+$).

$^1$H-NMR (CDCl$_3$), δ: 5.17 (br s, 1H), 4.29 (t, 1H, J=5.5 Hz), 4.04–3.74 (m, 4H), 3.23 (dd, 1H, J=11.5, 7.0 Hz), 2.50 (t, 1H, J=11.5 Hz), 2.26–2.08 (m, 1H), 1.86 (s, 1H), 1.88–1.73 (m, 1H), 1.45 (s, 9H).

Example C (+)-(1R*,5S*,8R*)-8-(tert-butoxycarbonylamino)-2-oxa-6-azabicyclo[3.3.0]octane [a compound (II) in which R$_1$=Boc; R$_2$, R$_3$, R$_4$, R$_5$, R$_8$, R$_9$=H; m=0; n=1; and p=0] was obtained in substantially the same manner as described in Example A.

Melting point: 108–109° C.

IR (KBr), cm$^{-1}$: 3377, 3228, 1680.

$[\alpha]_D^{29}$=+44.5° (c=1.01, methanol).

$^1$H-NMR (CDCl$_3$), δ: 4.22 (d, 1H, J=5.5 Hz), 4.02–3.69 (m, 4H), 3.15 (d d, 1H, J=11.5, 5.0 Hz), 2.84 (dd, 1H, J=11.5, 3.0 Hz), 2.19–1.99 (m, 1H), 1.83–1.68 (m, 2H), 1.45 (s, 9H).

Example D (+)-(1R*,5S*,8S*)-8-(tert-butoxycarbonylamino)-2-oxa-6-azabicyclo[3.3.0]octane [a compound (II) in which R$_1$=Boc; R$_2$, R$_3$, R$_4$, R$_5$, R$_8$, R$_9$=H; m=0; n=1; and p=0] was obtained in substantially the same manner as described in Example B.

$[\alpha]_D^{28}$=+70.8° (c=1.00, methanol).

MS (m/z): 229 (MH$^+$).

$^1$H-NMR (CDCl$_3$), δ: 5.17 (br s, 1H), 4.29 (t, 1H, J=5.5 Hz), 4.04–3.74 (m, 4H), 3.23 (dd, 1H, J=11.5, 7.0 Hz), 2.50 (t, 1H, J=11.5 Hz), 2.26–2.08 (m, 1H), 1.86 (s, 1H), 1.88–1.73 (m, 1H), 1.45 (s, 9H).

Example E (1R*,6S*,9R*)-9-(tert-butoxycarbonylamino)-2-oxa-7-azabicyclo[4.3.0]nonane [a compound (II) in which R$_1$=Boc; R$_2$, R$_3$, R$_4$, R$_5$, R$_6$, R$_7$, R$_8$, R$_9$=H; m=0; n=1; and p=1].

Step 1

100 g of (3R*,4S*,5R*)-5-allyl-1-benzyl-3,4-bis(tert-butyidimethylsilyloxy)-2-pyrrolidinone which had been prepared according to the procedure described in J. Org. Chem. 60, 103–108 (1995) by using D-tartaric acid as the starting material was added to 670 ml of tetrahydrofuran, and cooled with ice. Then, 87.1 ml of a 1.0M solution of borane-tetrahydrofuran complex in tetrahydrofuran was added thereto. After this mixture was stirred at room temperature for 1 hour, 7 ml of water was added dropwise thereto, and 33.4 ml of a 5N aqueous solution of sodium hydroxide was added at a time. Then, 33.4 ml of a 30% aqueous solution of hydrogen peroxide was added thereto at such a rate as to give a reaction temperature of 30–50° C., followed by stirring overnight. Thereafter, water and ethyl acetate were added to the reaction mixture so as to extract the product in an organic layer. After this organic layer was dried over anhydrous magnesium sulfate, the solvent was distilled off under reduced pressure. The resulting residue was purified by silica gel column chromatography (using chloroform as the eluent) to obtain 33.4 g of (3R*,4S*,5R*)-1-benzyl-3,4-bis(tert-butyidimethylsilyloxy)-5-(3-hydroxypropyl)-2-pyrrolidinone.

IR (neat), cm$^{-1}$: 3444, 1697.

MS (m/z): 494 (MH$^+$).

$^1$H-NMR (CDCl$_3$), δ: 7.40–7.20 (m, 5H), 4.86 (d, 1H, J=15.0 Hz), 4.20 (d, 1H, J=6.0 Hz), 4.12 (d, 1H, J=15.0 Hz), 4.12–4.06 (m, 1H), 3.65–3.40 (m, 3H), 1.75–1.25 (m, 4H), 0.95 (S, 9H), 0.90 (s, 9H), 0.23 (s, 3H), 0. 17(s, 3H), 0.10 (s, 3H), 0.02 (s, 3H).

Step 2

33.4 g of the compound obtained in the preceding step 1 and 10.3 g of triethylamine were added to 400 ml of methylene chloride, and cooled with ice. Then, 15.5 g of p-toluenesulfonyl chloride was added thereto, followed by stirring for 1.5 days. Thereafter, water and chloroform were added thereto so as to extract the product in an organic layer. After this organic layer was washed with water and then dried over anhydrous magnesium sulfate, the solvent was distilled off under reduced pressure. The resulting residue was purified by silica gel column chromatography (using a 5:1 mixture of n-hexane and ethyl acetate as the eluent) to obtain 32.8 g of (3R*,4S*,5R*)-1-benzyl-3,4-bis(tert-butyldimethylsilyloxy)-5-(3-tosyloxypropyl)-2-pyrrolidinone.

IR (neat), cm$^{-1}$: 1715, 1360, 1254, 1176.

MS (m/z): 648 (MH$^+$).

$^1$H-NMR (CDCl$_3$), δ: 7.80–7.73 (m, 2H), 7.39–7.19 (m, 7H), 4.82 (d, 1H, J=15.0 Hz), 4.15–4.07 (m, 2H), 4.00 (d, 1H, J=15.0 Hz), 3.91–3.83 (m, 2H), 3.45–3.35 (m, 1H), 2.47 (s, 3H), 1.70–1.25 (m, 4H), 0.95 (s, 9H), 0.84 (s, 9H), 0.22 (s, 3H), 0.15 (s, 3H), 0.08 (s, 3H), −0.03 (s, 3H).

Step 3

32.8 g of the compound obtained in the preceding step 2 was added to 500 ml of tetrahydrofuran. Then, 60.7 ml of a 1.0M solution of tetra-n-butylammonium fluoride in tetrahydrofuran was added thereto, followed by heating under reflux for 30 minutes. Thereafter, water and ethyl acetate were added to the reaction mixture so as to extract the product in an organic layer. After this organic layer was dried over anhydrous magnesium sulfate, the solvent was distilled off under reduced pressure. The resulting residue was purified by silica gel column chromatography (using a 30:1 mixture of chloroform and methanol as the eluent) to obtain 10.6 g of (1R*,6S*,9S*)-7-benzyl-9-hydroxy-8-oxo-2-oxa-7-azabicyclo[4.3.0]nonane.

Melting point: 136–138° C.
IR (KBr), $cm^{-1}$: 3295, 1664.
MS (m/z): 248 (MH$^+$).
$[\alpha]_D^{30}$=−90.6° (c=1.00, methanol).
$^1$H-NMR (CDCl$_3$), δ: 7.40–7.20 (m, 5H), 4.88 (d, 1H, J=15.0 Hz), 4.40 (dd, 1H, J=2.8, 5.0 Hz), 4.18 (d, 1H, J=15.0 Hz), 4.05 (t, 1H, J=5.0 Hz), 3.82–3.68 (m, 1H), 3.65–3.46 (m, 2H), 3.40 (d, 1H, J=2.8 Hz), 1.97–1.78 (m, 1H), 1.73–1.30 (m, 3H).

Step 4

12.5 g of the compound obtained in the preceding step 3 was treated in the same manner as described in the step 3(1) of Example A. Thus, there was obtained 11.9 g of (1R*,6S*,9R*)-9-acetoxy-7-benzyl-8-oxo-2-oxa-7-azabicyclo[4.3.0]nonane.

IR (neat), $cm^{-1}$: 3564, 1715, 1230.
MS (m/z): 290 (MH$^+$).
$^1$H-NMR (CDCl$_3$), δ: 7.40–7.20 (m, 5H), 5.29 (d, 1H, J=4.2 Hz), 4.95 (d, 1H, J=15.0 Hz), 4.28 (dd, 1H, J=2.5, 4.5 Hz), 4.13 (d, 1H, J=15.0 Hz), 3.98–3.86 (m, 1H), 3.44–3.37 (m, 1H), 3.33 (dt, 1H, J=2.5, 11.1 Hz), 2.38 (s, 3H), 2.38–2.20 (m, 1H), 1.74–1.25 (m, 3H).

Step 5

11.9 g of the compound obtained in the preceding step 4 was treated in the same manner as described in the step 3(2) of Example A. Thus, there was obtained 10.8 g of (1R*,6S*,9R*)-7-benzyl-9-hydroxy-8-oxo-2-oxa-7-azabicyclo[4.3.0]nonane.

Melting point: 163–165° C. (recrystallized from methylene chloride-n-hexane).
IR (KBr), $cm^{-1}$: 3340, 1692.
MS (m/z): 248 (MH$^+$).
$[\alpha]_D^{30}$=−55.7° (c=1,00, methanol).
$^1$H-NMR (CDCl$_3$), δ: 7.40–7.20 (m, 5H), 5.00 (d, 1H, J=15.0 Hz), 4.26 (br, 1H), 4.11 (dd, 1H, J=2.8, 4.2 Hz), 4.05 (d, 1H, J=15.0 Hz), 4.00–3.90 (m, 1H), 3.48–3.32 (m, 2H), 2.89 (br, 1H), 2.25–2.20 (m, 1H), 1.70–1.30 (m, 3H).

Step 6

10.6 g of the compound obtained in the preceding step 5 was treated in the same manner as described in the step 4 of Example A. Thus, there was obtained 9.3 g of (1R*,6S*,9S*)-9-azido-7-benzyl-8-oxo-2-oxa-7-azabicyclo[4.3.0]nonane.

IR (neat), $cm^{-1}$: 2107, 1698.
MS (m/z): 273 (MH$^+$).
$^1$H-NMR (CDCl$_3$), δ: 7.40–7.20 (m, 5H), 4.95 (d, 1H, J=15.0 Hz), 4.15 (d, 1H, J=3.9 Hz), 4.06 (d, 1H, J=15.0 Hz), 3.91–3.72 (m, 2H), 3.56–3.41 (m, 2H), 1.94–1.25 (m, 4H).

Step 7

9.2 g of the compound obtained in the preceding step 6 was treated in the same manner as described in the step 5(1) of Example A. Thus, there was obtained 7.3 g of (1R*,6R*,9S*)-9-amino-7-benzyl-2-oxa-7-azabicyclo[4.3.0]nonane.

IR (neat), $cm^{-1}$: 3372.
MS (m/z): 233 (MH$^+$).
$^1$H-NMR (CDCl$_3$), δ: 7.38–7.18 (m, 5H), 4.01 (d, 1H, J=15.0 Hz), 3.90–3.87 (m, 1H) 3.58 (d, 1H, J=3.6 Hz), 3.50–3.25 (m, 3H), 3.28 (d, 1H, J=15.0 Hz), 2.62 (dd, 1H, J=6.8, 3.8 Hz), 2.15–1.92 (m, 2H), 1.86 (dd, 1H, J=10.0, 5.0 Hz), 1.80–1.60 (m, 1H), 1.42–1.12 (m, 3H).

Step 8

7.2 g of the compound obtained in the preceding step 7 was treated in the same manner as described in the step 5(2) of Example A. Thus, there was obtained 10.1 g of (1R*,6R*,9S*)-7-benzyl-9-(tert-butoxycarbonylamino)-2-oxa-7-azabicyclo[4.3.0]nonane.

Melting point: 120–123° C.
IR (KBr), $cm^{-1}$: 3367, 1683.
MS (m/z): 333 (MH$^+$).
$[\alpha]_D^{30}$=+57.8° (c=1.01, methanol).
$^1$H-NMR (CDCl$_3$), δ: 7.38–7.20 (m, 5H), 4.38 (br, 1H), 4.05–3.72 (m, 4H), 3.56–3.22 (m, 3H), 2.60–2.47 (m, 1H), 2.08–1.84 (m, 3H), 1.80–1.64 (m, 1H), 1.42 (s, 9H), 1.39–1.23 (m, 1H).

Step 9

7.4 g of the compound obtained in the preceding step 8 was treated in the same manner as described in the step 6 of Example A. Thus, 4.2 g of the desired (1R*,6S*,9R*)-9-(tert-butoxycarbonylamino)-2-oxa-7-azabicyclo[4.3.0]nonane was obtained.

Melting point: 110–111° C. (recrystallized from methylene chloride-n-hexane).
IR (KBr), $cm^{-1}$: 3311, 1711, 1687.
MS (m/z): 243 (MH$^+$).
$[\alpha]_D^{30}$=+2.4° (c=1.00, methanol).
$^1$H-NMR (CDCl$_3$), δ: 4.53 (br, 1H), 3.98–3.80 (m, 2H), 3.74–3.55 (m, 2H), 3.36 (dt, 1H, J=11.5, 2.5 Hz), 3.01–2.92 (m, 1H), 2.55 (dd, 1H, J=12.5, 3.8 Hz), 2.20–1.58 (m, 5H), 1.44 (s, 9H).

Example F (1R*,6S*,9S*)-9-(tert-butoxycarbonylamino)-2-oxa-6-azabicyclo[4.3.0]nonane [a compound (II) in which $R_1$=Boc; $R_2$, $R_3$, $R_4$, $R_5$, $R_6$, $R_7$, $R_8$, $R_9$=H; m=0; n=1; and p=1].

Step 1

10.6 g of the (1R*,6S*,9S*)-7-benzyl-9-hydroxy-8-oxo-2-oxa-7-azabicyclo[4.3.0]nonane obtained in the step 3 of Example E was treated in the same manner as described in the step 4 of Example A. Thus, there was obtained 9.3 g of (1R*,6S*,9R*)-9-azido-7-benzyl-8-oxa-2-oxa-7-azabicyclo[4.3.0]nonane.

IR (neat), $cm^{-1}$: 2108, 1694.
MS (m/z): 273 (MH$^+$).
$^1$H-NMR (CDCl$_3$), δ: 7.40–7.20 (m, 5H), 5.02 (d, 1H, J=15.0 Hz), 4.15 (dd, 1H, J=2.7, 4.2 Hz), 4.07 (d, 1H, J=15.0 Hz), 4.04–3.92 (m, 1H), 3.87 (d, 1H, J=4.2 Hz), 3.46–3.31 (m, 2H), 2.26–2.12 (m, 1H), 1.73–1.28 (m, 3H)

Step 2

9.3 g of the compound obtained in the preceding step 1 was treated in the same manner as described in the step 5(1) of Example A. Thus, there was obtained 7.2 g of (1R*,6R*,9R*)-9-amino-7-benzyl-2-oxa-7-azabicyclo[4.3.0]nonane.

IR (neat), $cm^{-1}$: 3365.
MS (m/z): 233 (MH$^+$).
$^1$H-NMR (CDCl$_3$), δ: 7.40–7.18 (m, 5H), 4.10–3.97 (m, 1H), 3.93 (d, 1H, J=15.0 Hz), 3.66 (dd, 1H, J=4.2, 2.5 Hz), 3.52–3.33 (m, 3H), 2.21–1.52 (m, 5H), 1.40–1.24 (m, 1H).

Step 3

7.2 g of the compound obtained in the preceding step 2 was treated in the same manner as described in the step 5(2)

of Example A. Thus, there was obtained 9.5 g of (1R*,6R*,9R*)-7-benzyl-9-(tert-butoxycarbonylamino)-2-oxa-7-azabicyclo[4.3.0]nonane.

Melting point: 82–84° C.
IR (KBr), cm$^{-1}$: 3446, 1711.
MS (m/z): 333 (MH$^+$).
[α]$_D^{30}$=+41.3° (c=1.00, methanol).
$^1$H-NMR (CDCl$_3$), δ: 7.38–7.15 (m, 5H), 5.21 (br d, 1H, J=8.3 Hz), 4.27–4.09 (m, 1H), 4.07–3.96 (m, 1H), 3.94 (d, 1H, J=15.0 Hz), 3.83 (dd, 1H, J=4.8, 2.5 Hz), 3.51–3.34 (m, 1H), 3.33 (d, 1H, J=15.0 Hz), 2.92–2.64 (m, 3H), 2.21–1.88 (m, 2H), 1.74–1.24 (m, 2H), 1.40 (s, 9H)

Step 4

9.1 g of the compound obtained in the preceding step 3 was treated in the same manner as described in the step 6 of Example A. Thus, 5.9 g of the desired (1R*,6S*,9S*)-9-(tert-butoxycarbonylamino)-2-oxa-7-azabicyclo[4.3.0]nonane was obtained.

IR (neat), cm$^{-1}$: 3451, 1710, 1170.
MS (m/z): 243 (MH$^+$).
[α]$_D^{30}$=−41.1° (c=1.03, methanol).
$^1$H-NMR (CDCl$_3$), δ: 5.17 (br, 1H), 4.30–4.10 (m, 1H), 4.01–3.87 (m, 1H), 3.69 (dd, 1H, J=4.2, 2.2 Hz), 3.44–3.22 (m, 2H), 3.08 (br, 1H), 2.84 (dd, 1H, J=11.0, 7.2 Hz), 2.00–1.70 (m, 5H), 1.45 (s, 9H).

Example G (1R*,5S*,8R*)-8-(N-tert-butoxycarbonylmethylamino)-2-oxa-6-azabicyclo[3.3.0]octane [a compound (II) in which R$_1$=Boc; R$_2$=Me; R$_3$, R$_4$, R$_5$, R$_8$, R$_9$=H; m=0; n=1; and p=0].

Step 1

36.7 g of a 70% solution of sodium bis(2-methoxyethoxy)aluminum hydride in toluene was dissolved in 120 ml of toluene, and cooled with ice. Then, 8.1 g of the (1R*,5R*,8S*)-6-benzyl-8-(tert-butoxycarbonylamino)-2-oxa-6-azabicyclo[3.3.0]octane obtained in the step 5(2) of Example A was added thereto, and this mixture was slowly heated to 100° C. and stirred for 2 hours. After cooling with ice, any excess reagent was decomposed by the addition of ice. Then, a 10% aqueous solution of sodium hydroxide was added thereto, and the product was extracted with ethyl acetate. After the extract was dried over anhydrous magnesium sulfate, the solvent was distilled off under reduced pressure. Then, 150 ml of methanol and 7.2 g of di-tert-butyl dicarbonate were added to the resulting residue, followed by stirring at room temperature overnight. After the reaction mixture was concentrated under reduced pressure, the resulting residue was purified by silica gel column chromatography (using a 5:1 mixture of n-hexane and ethyl acetate as the eluent) to obtain 8.1 g of (1R*,5S*,8R*)-6-benzyl-8-(N-tert-butoxycarbonylmethylamino)-2-oxa-6-azabicyclo[3.3.0]octane.

IR (neat), cm$^{-1}$: 2972, 1698.
MS (m/z): 333 (MH$^+$).
$^1$H-NMR (CDCl$_3$), δ: 7.38–7.20 (m, 5H), 4.63 (dd, 1H, J=6.5, 4.5 Hz), 4.18–4.02 (m, 1H), 3.98–3.80 (m, 3H), 3.41 (d, 1H, J=13.0 Hz), 3.35–3.25 (m, 1H), 2.95 (dd, 1H, J=9.0, 7.5 Hz), 2.85 (s, 3H), 2.42 (dd, 1H, J=10.0, 9.0 Hz), 1.86–1.59 (m, 2H), 1.43 (s, 9H).

Step 2

8.1 g of the compound obtained in the preceding step 1 was dissolved in 150 ml of ethanol, and 800 mg of 5% palladium-carbon was added thereto. Then, this mixture was made to absorb a stoichiometric amount of hydrogen at 40° C. After the catalyst was removed by filtration, the solvent was distilled off under reduced pressure to obtain 5.9 g of the desired (1R*,5S*,8R*)-8-(N-tert-butoxycarbonylmethylamino)-2-oxa-6-azabicyclo[3.3.0]octane.

IR (neat), cm$^{-1}$: 3348, 2973, 1682.
MS (m/z): 243 (MH$^+$).
[α]$_D^{30}$=−56.3° (c=1.05, methanol).
$^1$H-NMR (CDCl$_3$), δ: 4.52 (dd, 1H, J=6.0, 3.0 Hz), 4.11 (dt, 1H, J=7.5, 3.0 Hz), 3.97–3.74 (m, 3H), 3.21 (dd, 1H, J=11.0, 7.5 Hz), 2.97 (dd, 1H, J=11.0, 7.5 Hz), 2.87 (s, 3H), 2.11–1.91 (m, 1H), 1.83–1.67 (m, 1H), 1.73 (br s, 1H), 1.46 (s, 9H).

Example H (1R*,5S*,8S*)-8-(N-tert-butoxycarbonylmethylamino)-2-oxa-6-azabicyclo[3.3.0]octane [a compound (II) in which R$_1$=Boc; R$_2$=Me; R$_3$, R$_4$, R$_5$, R$_8$, R$_9$=H; m=0; n=1: and p=0].

Step 1

(1R*,5S*,8S*)-6-benzyl-8-(N-tert-butoxycarbonylmethylamino)-2-oxa-6-azabicyclo[3.3.0]octane was obtained in substantially the same manner as described in the step 1 of Example G.

IR (neat), cm$^{-1}$: 1682.
MS (m/z): 333 (MH$^+$).
$^1$H-NMR (CDCl$_3$), δ: 7.20–7.38 (m, 5H), 4.47–4.56 (m, 1H), 4.00–3.84 (m, 2H), 3.95 (d, 1H, J=15.0 Hz), 3.30 (d, 1H, J=15.0 Hz), 3.25–3.17 (m, 1H), 2.94–2.85 (m, 1H), 2.85 (m, 3H), 2.52–2.35 (m, 1H), 2.05–1.72 (m, 3H), 1.45 (s, 9H).

Step 2

9.5 g of the compound obtained in the preceding step 1 was treated in substantially the same manner as described in the step 2 of Example G. Thus, 5.0 g of the desired (1R*,5S*,8S*)-8-(N-tert-butoxycarbonylmethylamino)-2-oxa-6-azabicyclo[3.3.0]octane was obtained.

IR (neat) cm$^{-1}$: 1692.
MS (m/z): 243 (MH$^+$).
$^1$H-NMR (CDCl$_3$), δ: 4.39 (t, 1H, J=5.0 Hz), 4.29–4.10 (br, 1H), 3.98–3.70 (m, 3H), 2.99 (d, 2H, J=9.0 Hz), 2.93 (s, 3H), 2.25–2.07 (m, 1H), 1.88–1.74 (m, 1H), 1.73–1.64 (br, 1H), 1.48 (s, 9H).

Example J (1R*,5S*,8R*)-8-trifluoroacetylamino-2-oxa-6-azabicyclo[3.3.0]octane [a compound (II) in which R$_1$=COCF$_3$; R$_2$, R$_3$, R$_4$, R$_5$, R$_8$, R$_9$=H; m=0; n=1; and p=0].

Step 1

4.8 g of the (1R*,5R*,8S*)-8-amino-6-benzyl-2-oxa-6-azabicyclo[3.3.0]octane obtained in the step 5(1) of Example A was added to 150 ml of methylene chloride, and cooled with ice. Then, a solution of 6.9 g of trifluoroacetic acid anhydride in 50 ml of methylene chloride was slowly added thereto, followed by stirring overnight. Thereafter, chloroform was added to the reaction mixture so as to extract the product in an organic layer. After the organic layer was dried over anhydrous magnesium sulfate, the solvent was distilled off under reduced pressure. The resulting residue was purified by silica gel column chromatography (using a 1:1 mixture of n-hexane and ethyl acetate as the eluent) to obtain crude crystals. These crystals were recrystallized from a mixture of methylene chloride and n-hexane to obtain 4.7 g of (1R*,5R*,8S*)-6-benzyl-8-trifluoroacetylamino-2-oxa-6-azabicyclo[3.3.0]octane.

Melting point: 150–154° C.
IR (KBr), cm$^{-1}$: 3305, 1702, 1180.
MS (m/z): 315 (MH$^+$)
[α]$_D^{30}$=−4.6° (c=1.00, methanol)
$^1$H-NMR (CDCl$_3$), δ: 7.40–7.20 (m, 5H), 6.50 (br, 1H), 4,34 (dd, 1H, J=7.0, 4.0 Hz), 4.25–4.11 (m, 1H), 3.98–3.76

(m, 3H), 3.58–3.46 (m, 2H), 3.15 (dd, 1H, J=9.5, 6.0 Hz), 2.33 (dd, 1H, J=9.5, 7.0 Hz), 1.94–1.64 (m, 2H).
Step 2

6.0 g of the compound obtained in the preceding step 1 was dissolved in 100 ml of ethanol, and 600 mg of 10% palladium-carbon was added thereto. Then, this mixture was made to absorb a stoichiometric amount of hydrogen at 50–60° C. After the catalyst was removed by filtration, the solvent was distilled off under reduced pressure. The resulting crystals were recrystallized from chloroform-n-hexane to obtain 4.0 g of the desired (1R*,5S*,8R*)-8-trifluoroacetylamino-2-oxa-6-aza bicyclo[3.3.0]octane.

Melting point: 106–110° C.
IR (KBr), cm$^{-1}$: 3319, 1706, 1559, 1180.
MS (m/z): 225 (MH$^+$).
$[\alpha]_D^{30}$=−40.5° (c=1.00, methanol).
$^1$H-NMR (CDCl$_3$), δ: 6.69 (br, 1H), 4,34–4.21 (m, 2H), 4.08–3.72 (m, 3H), 3.28 (dd, 1H, J=11.0, 5.0 Hz), 2.90 (ddd, 1H, J=11.0, 3.5, 1.0 Hz), 2.24–2.05 (m, 1H), 1.85–1.68 (m, 2H).

Example K (1R*,5S*,8S*)-8-(tert-butoxycarbonylamino)-3-methyl-2-oxa-6-azabicyclo[3.3.0]octane [a compound (II) in which R$_1$ =Boc; R$_2$, R$_3$, R$_5$, R$_8$, R$_9$=H; R$_4$=Me; m=0; n=1; and p=0].
Step 1

A mixture composed of 150 g of (3R*,4S*,5R*)-5-allyl-1-benzyl-3,4-bis(tert-butyldimethylsilyloxy)-2-pyrrolidinone which had been prepared according to the procedure described in J. Org. Chem. 60, 103–108 (1995) by using D-tartaric acid as the starting material, 500 ml of ethanol, and 20 ml of concentrated hydrochloric acid was heated to 50° C. and stirred for 2 days. After the reaction mixture was concentrated under reduced pressure, water was added to the resulting residue. This mixture was washed with n-hexane and then extracted with chloroform. After the extract was dried over anhydrous magnesium sulfate, the solvent was distilled off under reduced pressure. Then, ether and n-hexane were added to the resulting residue so as to crystallize the desired product. These crystals were collected by filtration to obtain 24.8 g of (3R*,4S*,5R*)-5-allyl-1-benzyl-3,4-dihydroxy-2-pyrrolidinone.

Melting point: 90–93° C.
IR (KBr), cm$^{-1}$: 3345, 1682.
MS (m/z): 248 (MH$^+$).
$^1$H-NMR (CDCl$_3$), δ: 7.38–7.14 (m, 5H), 5.92–5.64 (m, 1H), 5.27–4.95 (m, 4H), 4.53–4.14 (m, 3H), 3.99 (d, 1H, J=15.0 Hz), 3.62–3.47 (m, 1H), 2.60–2.26 (m, 2H).
Step 2

15 g of the compound obtained in the preceding step 1, 45 g of sodium iodide, and 5 g of 18-crown-6 were dissolved in 500 ml of methylene chloride. While this mixture was being vigorously stirred under cooling with ice, 500 ml of a methylene chloride solution containing 19.5 g of m-chloroperbenzoic acid was slowly added dropwise thereto, followed by stirring at room temperature overnight. Thereafter, chloroform and aqueous sodium hydroxide were added to the reaction mixture so as to extract the desired product in an organic layer. After this organic layer was washed with an aqueous solution of sodium thiosulfate and then dried over anhydrous magnesium sulfate, the solvent was distilled off under reduced pressure. The resulting residue was purified by silica gel column chromatography (using a 30:1 mixture of chloroform and methanol as the eluent) to obtain 13.8 g of (1R*,5S*,8S*)-6-benzyl-8-hydroxy-3-iodomethyl-7-oxo-2-oxa-6-azabicyclo[3.3.0]octane.

IR (neat) cm$^{-1}$: 3364, 1682.
MS (m/z): 374 (MH$^+$).
$^1$H-NMR (CDCl$_3$), δ: 7.41–7.19 (m, 5H), 4.93 (d, J=14.5 Hz)+4.88 (d, J=14.5 Hz) (1H), 4.64–4.32 (m, 2H), 4.26–3.84 (m, 3H), 3.52 (br s, 1H), 3.30–3.12 (m, 2H), 2.30–2.13 (m, 1H), 1.74–1.54 (m, 1H).
Step 3

14 g of the compound obtained in the preceding step 2 was dissolved in 200 ml of methanol, and 6.9 ml of triethylamine and 1.4 g of 5% palladium-carbon were added thereto. Then, this mixture was made to absorb a stoichiometric amount of hydrogen at room temperature. After the catalyst was removed by filtration, the solvent was distilled off under reduced pressure. Thereafter, water and chloroform were added to the resulting residue so as to extract the desired product in an organic layer. After this organic layer was washed with a dilute aqueous solution of hydrochloric acid and with water and then dried over anhydrous magnesium sulfate, the solvent was distilled off under reduced pressure to obtain 10.9 g of (1R*,5S*,8S*)-6-benzyl-8-hydroxy-3-methyl-7-oxo-2-oxa-6-azabicyclo[3.3.0]octane.

IR (neat), cm$^{-1}$: 3351, 1682.
MS (m/z): 248 (NH+).
$^1$H-NMR (CDCl$_3$), δ: 7.41–7.18 (m, 5H), 4.90 (d, 1H, J=15.0 Hz), 4.45–4.31 (m, 3H), 4.18–3.87 (m, 3H), 2.20–1.95 (m, 1H), 1.48–1.20 (m, 4H).
Step 4

8.4 g of the compound obtained in the preceding step 3 was treated in substantially the same manner as described in the step 4 of Example A. Thus, there was obtained 6.2 g of (1R*,5S*,8R*)-8-azido-6-benzyl-3-methyl-7-oxo-2-oxa-6-azabicyclo[3.3.0]octane.

IR (neat), cm 2108, 1694.
MS (m/z): 273 (MH$^+$).
$^1$H-NMR (CDCl$_3$), δ: 7.41–7.18 (m, 5H), 5.05 (d, J=15.0 Hz)+4.98 (d, J=15.0 Hz) (1H), 4.67 (dd, J=5.0, 6.0 Hz)+4.44 (t, J=6.0 Hz) (1H), 4.24–3.87 (m, 4H), 2.32–2.11 (m, 1H), 1.74–1.39 (m, 1H), 1.29 (d, J=6. 0 Hz)+1.27 (d, J=6.0 Hz) (3H).
Step 5

8.2 g of the compound obtained in the preceding step 4 was treated in substantially the same manner as described in the step 5 of Example A. Thus, there was obtained 10.1 g of (1R*,5R*,8R*)-6-benzyl-8-(tert-butoxycarbonylamino)-3-methyl-2-oxa-6-azabicyclo[3.3.0]octane.

IR (neat), cm$^{-1}$: 3447, 1714.
MS (m/z): 333 (MH$^+$).
$^1$H-NMR (CDCl$_3$), δ: 7.34–7.21 (m, 5H), 5.20 (br m, 1H), 4.57 (t, J=6.0 Hz)+4.35 (t, J=6.0 Hz) (1H), 4.26–3.28 (m, 5H), 2.99–2.45 (m, 2H), 2.09–1.60 (m, 2H), 1.44 (s, 9H), 1.32–1.21 (m, 3H).
Step 6

9.7 g of the compound obtained in the preceding step 5 was treated in substantially the same manner as described in the step 6 of Example A. Thus, 6.7 g of the desired (1R*,5S*,8S*)-8-(tert-butoxycarbonylamino)-3-methyl-2-oxa-6-azabicyclo[3.3.0]octane.

IR (neat), cm$^{-1}$: 3317, 1714.
MS (m/z): 243 (MH$^+$).
$^1$H-NMR (CDCl$_3$), δ: 5.16 (d, J=9.0 Hz)+5.18 (d, J=9.0 Hz) (1H), 4.19 (dd, J=6.6, 5.4 Hz)+4.44 (t, J=5.3 Hz) (1H), 3.99 (ddd, J=9.0, 6.6, 6.4 Hz)+3.98 (dd, J=6.6, 5.3 Hz) (1H), 3.84 (ddq, J=10.7, 5.2, 6.0 Hz)+4.10 (ddq, J=9.4, 4.8, 6.0 Hz) (1H), 3.80 (dddd, J=10.6, 9.0, 6.6, 5.4 Hz)+3.89 (dddd, J=10.0, 9.0, 7.1, 5.3 Hz) (1H), 3.16 (dd, J=11.3, 6.6 Hz)+3.28(dd, J=11.3, 7.1 Hz) (1H), 2.54 (dd, J=11.3, 10.6 Hz)+2.50 (dd, J=11.3, 10.0 Hz) (1H), 2.38 (ddd. J=12.9, 9.0, 5.2

Hz)+1.71 (ddd, J=12.9, 9.4, 6.6 Hz) (1H), 1.83 (s, 1H), 1.45 (s)+1.44 (s) (9H), 1.26 (d, J=6.0 Hz)+1.23 (d, J=6.0 Hz) (3H), 1.23 (ddd, J=12.9, 10.7, 6.4 Hz)+1.97 (dd, J=12.9, 4.8 Hz) (1H).

Example L (1R*,5S*,8R*)-8-(tert-butoxycarbonylamino)-3-methyl-2-oxa-6-azabicyclo[3.3.0]octane [a compound (II) in which $R_1$=Boc; $R_2$, $R_3$, $R_5$, $R_8$, $R_9$=H; $R_4$=Me; m=0; n=1; and p=0].

Step 1

8.7 g of the (1R*,5S*,8S*)-6-benzyl-8-hydroxy-3-methyl-7-oxo-2-oxa-6-azabicyclo[3.3.0]octane obtained in the step 3 of Example K was treated in the same manner as described in the step 3 of Example A. Thus, there was obtained 6.4 g of (1R*,5S*,8R*)-6-benzyl-8-hydroxy-3-methyl-7-oxo-2-oxa-6-azabicyclo[3.3.0]octane.

Melting point: 98–101° C.
IR (KBr), cm$^{-1}$: 3388, 1692.
MS (m/z): 248 (MH$^+$).
$^1$H-NMR (CDCl$_3$), δ: 7.40–7.15 (m, 5H), 5.03 (d, J=15.0 Hz)+4.95 (d, J=15.0 Hz) (1H), 4.60 (dd, J=5.0, 6.0 Hz)+4.46 (m) (5H), 3.17 (br d, J=6.0 Hz)+3.12 (br d, J=6.0 Hz) (1H), 2.32–2.10 (m, 1H), 1.73–1.39 (m, 1H), 1.26 (d, 3H, J=6.0 Hz)

Step 2

6.5 g of the compound obtained in the preceding step 1 was treated in the same manner as described in the step 4 of Example A. Thus, there was obtained 5.6 g of (1R*,5S*,8S*)-8-azido-6-benzyl-3-methyl-7-oxo-2-oxa-6-azabicyclo [3.3.0]octane.

Melting point: 70–73° C.
IR (KBr), cm$^{-1}$: 2122, 1690.
MS (m/z): 273 (MH$^+$).
$^1$H-NMR (CDCl$_3$), δ: 7.41–7.19 (m, 5H), 4.97 (d, 1H, J=15.0 Hz), 4.34 (dd, J=6.0, 1.5 Hz)+4.22–3.89 (m) (5H), 2.23–2.02 (m, 1H), 1.48–1.28 (m, 1H), 1.26 (d, J=6.0 Hz)+1.24 (d, J=6.0 Hz) (3H).

Step 3

5.6 g of the compound obtained in the preceding step 2 was treated in substantially the same manner as described in the step 5 of Example A. Thus, there was obtained 6.8 g of (1R*,5R*,8S*)-6-benzyl-8-(tert-butoxycarbonylamino)-3-methyl-2-oxa-6-azabicyclo[3.3.0]octane.

Melting point: 56–60° C.
IR (KBr), cm$^{-1}$: 3369, 1700.
MS (m/z): 333 (MH$^+$).

Step 4

6.8 g of the compound obtained in the preceding step 3 was treated in the same manner as described in the step 6 of Example A. Thus, 4.8 g of the desired (1R*,5S*,8R*)-8-(tert-butoxycarbonylamino)-3-methyl-2-oxa-6-azabicyclo [3.3.0]octane was obtained.

Melting point: 69–72° C.
IR (KBr), cm$^{-1}$: 3356, 1678.
MS (m/z): 243 (MH$^+$).
$^1$H-NMR (CDCl$_3$), δ: 4.78 (br s)+5.23 (br s) (1H), 4.10 (m)+4.37 (dd, J=5.5, 2.0 Hz) (1H), 4.00 (m)+3.95 (m) (1H), 3.90 (m)+3.95 (m) (1H), 3.79 (hep, J=6.0 Hz)+4.17 (m) (1H), 3.14 (dd, 1H, J=11.5, 4.5 Hz), 2.86 (br d, J=11.5 Hz)+2.80 (dd, J=11.5, 4.0 Hz) (1H), 2.33 (ddd, J=13.0, 8.5, 6.0 Hz)+1.90 (br dd, J=13.0, 5.0 Hz) (1H), 1.93 (s, 1H), 1.44 (s, 9H), 1.26 (d, J=6.0 Hz)+1.22 (d, J=6.0 Hz) (3H), 1.20 (ddd, J=13.0, 10.5, 6.0 Hz)+1.60 (ddd, J=13.0, 9.5, 6.5 Hz) (1H).

Example M (1R*,5R*)-8-(tert-butoxycarbonylaminomethyl)-2-oxa-6-azabicyclo[3.3.0]octane [a compound (II) in which $R_1$Boc; $R_2$, $R_3$, $R_4$, $R_5$, $R_8$, $R_9$=H; m1; n=1; and p=0].

Step 1

15 g of the (1R*,5S*,8S*)-6-benzyl-8-hydroxy-7-oxo-2-oxa-6-azabicyclo[3.3.0]octane obtained in the step 2 of Example A was added to 300 ml of methylene chloride, and cooled with ice. To this mixture was added 16.3 ml of triethylamine. Then, 7.5 ml of methanesulfonyl chloride was added dropwise thereto, followed by stirring overnight. Thereafter, water and methylene chloride were added to the reaction mixture so as to extract the desired product in an organic layer. After this organic layer was dried over anhydrous magnesium sulfate, the solvent was distilled off under reduced pressure to obtain 20.6 g of (1R*,5S*,8S*)-6-benzyl-8-mesyloxy-7-oxo-2-oxa-6-azabicyclo[3.3.0]octane.

IR (neat), cm$^{-1}$: 1714.
MS (m/z): 312 (MH$^+$).
$^1$H-NMR (CDCl$_3$), δ: 7.42–7.20 (m, 5H), 5.08 (d, 1H, J=1.5 Hz), 4.91 (d, 1H, J=15.0 Hz), 4.61 (dd, 1H, J=6.0, 1.5 Hz), 4.21–4.10 (m, 1H), 4.12 (d, 1H, 15.0 Hz), 3.98–3.68 (m, 2H), 3.28 (s, 3H), 1.99–1.81 (m, 2H).

Step 2

23.6 g of the compound obtained in the preceding step 1, 26 g of sodium cyanide, and 40.2 g of 18-crown-6 were added to 800 ml of acetonitrile. This mixture was heated to 45° C. and stirred for 5 days. After the reaction mixture was concentrated under reduced pressure, ethyl acetate and water were added to the resulting residue so as to extract the desired product in an organic layer. After this organic layer was dried over anhydrous magnesium sulfate, the solvent was distilled off under reduced pressure. The resulting residue was purified by silica gel column chromatography (using a 1:1 mixture of n-hexane and ethyl acetate as the eluent) to obtain 6.3 g of (1R*,5R*)-6-benzyl-8-cyano-7-oxo-2-oxa-6-azabicyclo[3.3.0]octane.

IR (neat), cm$^{-1}$: 2210, 1714.
MS (m/z): 242 (MH$^+$).
$^1$H-NMR (CDCl$_3$), δ: 7.45–7.22 (m, 5H), 4.95 (d, 1H, 15.0 Hz), 4.77 (dd, 1H, J=7.0, 1.6 Hz), 4.31 (d, 1H, J=15.0 Hz), 3.94–3.67 (m, 2H), 2.94 (dd, J=7.0, 0.7 Hz)+2.85 (dd, J=7.0, 0.7 Hz) (1H), 2.69 (d, J=1.6 Hz)+2.60 (d, J=1.6 Hz) (1H), 2.27–1.96 (m, 2H).

Step 3

6.3 g of the compound obtained in the preceding step 2 was added to 200 ml of tetrahydrofuran, and cooled with ice. Then, 104 ml of a 1.0M solution of borane-tetrahydrofuran complex in tetrahydrofuran was added thereto. This mixture was heated after 30 minutes and refluxed overnight. After the reaction mixture was cooled to room temperature, any excess reagent was decomposed by treatment with ethanol. After the reaction mixture was concentrated under reduced pressure, 500 ml of ethanol was added to the resulting residue, followed by refluxing overnight. After the reaction mixture was concentrated under reduced pressure, a 10% aqueous solution of hydrochloric acid was added to the resulting residue so as to extract the product in an aqueous layer. This aqueous layer was washed with ethyl acetate, alkalified by the addition of a 20% aqueous solution of sodium hydroxide, and then extracted with chloroform. After the extract was dried over anhydrous magnesium sulfate, the solvent was distilled off under reduced pressure. The resulting residue was added to 200 ml of methanol, followed by cooling with ice. Then, 6.8 g of di-tert-butyl dicarbonate was added thereto, followed by stirring at room temperature overnight. After the reaction mixture was concentrated under reduced pressure, the resulting residue was purified by silica gel column chromatography (using a 2:1 mixture of n-hexane and ethyl acetate as the eluent) to obtain 2.7 g of (1R*,5R*)-6-benzyl-8-(tert-butoxycarbonylaminomethyl)-2-oxa-6-azabicyclo[3.3.0] octane.

IR (neat), cm$^{-1}$: 3359, 1714.

MS (m/z): 333 (MH$^+$).

$^1$H-NMR (CDCl$_3$), δ: 7.30 (m, 5H), 5.12 (br d, 1H, J=9.0 Hz), 4.18 (br d, 1H, J=5.5 Hz), 3.98 (ddd, 1H, J=9.0, 7.7, 3.0 Hz), 3.77 (d, 1H, J=13.0 Hz), 3.67 (ddd, 1H, J=9.7, 9.0, 5.5 Hz), 3.50 (br dd, 1H, J=13.5, 9.0 Hz), 3.35 (d, 1H, J=13.0 Hz), 3.14 (dd, 1H, J=13.5, 1.8 Hz), 2.80 (m, 1H), 2.50 (dd, J=10.8, 6.0 Hz)+2.46 (dd, J=10.0, 7.1 Hz) (1H), 2.14 (ddd, 1H, J=12.5, 9.7, 7.5 Hz), 1.70 (m, 2H), 1.50 (m, 1H), 1.46 (s, 9H).

Step 4

2.7 g of the compound obtained in the preceding step 3 was dissolved in 100 ml of ethanol, and 0.25 g of 5% palladium-carbon was added thereto. Then, this mixture was heated to 50° C. and made to absorb a stoichiometric amount of hydrogen. After the catalyst was removed by filtration, the solvent was distilled off under reduced pressure to obtain 1.8 g of the desired (1R*,5R*)-8-(tert-butoxycarbonylaminomethyl)-2-oxa-6-azabicyclo[3.3.0] octane.

Melting point: 59–67° C.

IR (KBr), cm$^{-1}$: 3447, 1697.

MS (m/z): 243 (MH$^+$).

$^1$H-NMR (CDCl$_3$), δ: 5.00 (br s, 1H), 4.11 (m, 1H), 3.94 (m, 1H), 3.73 (m, 1H), 3.25 (m, 2H), 3.07 (m, 1H), 2.98 (m, 1H), 2.03 (m, 1H), 1.90 (m)+1.88 (m) (1H), 1.80 (m, 1H), 1.77 (m, 1H), 1.63 (br s, 1H), 1.44 (s, 9H).

Example 1

7-[(1R*,5R*,8S*)-8-amino-2-oxa-6-azabicyclo[3.3.0] oct-6-yl]-1-cyclopropyl-6-fluoro-1,4-dihydro-8-methoxy-4-oxoquinoline-3-carboxylic acid.

(1) 0.96 g of the (1R*,5S*,8R*)-8-(tert-butoxycarbonylamino)-2-oxa-6-azabicyclo[3.3.0]octane obtained in Example A, 1.2 g of 1-cyclopropyl-6,7-difluoro-1,4-dihydro-8-methoxy-4-oxoquinoline-3-carboxylic acid-BF$_2$ chelate, and 0.69 ml of triethylamine were added to 13 ml of dimethyl sulfoxide, followed by stirring at room temperature for 5 days. Thereafter, water was added to the reaction mixture and the crystals so precipitated were collected by filtration. To these crystals were added 60 ml of ethanol, 1 ml of water, and 2 ml of triethylamine. This mixture was heated to 80° C. and stirred overnight. After the reaction mixture was concentrated under reduced pressure, water and chloroform were added to the resulting residue so as to extract the product in an organic layer. After the extract was dried over anhydrous magnesium sulfate, the solvent was distilled off under reduced pressure to obtain 1.65 g of 7-[(1R*,5R*,8S*)-8-(tert-butoxycarbonylamino)-2-oxa-6-azabicyclo[3.3.0]oct-6-yl]-1-cyclopropyl-6-fluoro-1,4-dihydro-8-methoxy-4-oxoquinoline-3-carboxylic acid.

(2) 1.65 g of the compound obtained in the preceding step (1) was dissolved in 4 ml of ethanol, and 15 ml of a 10% aqueous solution of hydrochloric acid was added thereto. This mixture was heated at 80° C. for 3.5 hours with stirring. After the solvent was distilled off under reduced pressure, all reactants were dissolved by the addition of a 10% aqueous solution of hydrochloric acid, and this solution was washed with chloroform. Subsequently, after the hydrochloric acid was removed under reduced pressure as much as possible, the solution was alkalified by the addition of concentrated aqueous ammonia. Thus, all reactants were dissolved and this solution was washed again with chloroform. After the ammonia was removed under reduced pressure as much as possible, the solution was neutralized to pH 7 with a dilute aqueous solution of hydrochloric acid, and chloroform was added thereto so as to extract the product in an organic layer. After this organic layer was dried over anhydrous magnesium sulfate, the solvent was distilled off under reduced pressure to obtain crude crystals. These crystals were recrystallized from a mixture of methylene chloride and ethyl acetate to obtain the desired 7-[(1R*,5R*,8S*)-8-amino-2-oxa-6-azabicyclo[3.3.0]oct-6-yl]-1-cyclopropyl-6-fluoro-1,4-dihydro-8-methoxy-4-oxoquinoline-3-carboxylic acid.

Melting point: 187–189° C.

Example 2

The following compound was obtained in substantially the same manner as described in Example 1.

7-[(1R*,5R*,8S*)-8-amino-2-oxa-6-azabicyclo[3.3.0] oct-6-yl]-6-fluoro-1-[(1R,2S)-2-fluorocyclopropyl]-1,4-dihydro-8-methoxy-4-oxoquinoline-3-carboxylic acid.

Melting point: 184–187° C.

Example 3

5-Amino-7-[(1R*,5R*,8S*)-8-amino-2-oxa-6-azabicyclo [3.3.0]oct-6-yl]-1-cyclopropyl-6,8-difluoro-1,4-dihydro-4-oxoquinoline-3-carboxylic acid.

(1) A mixture composed of 1.5 g of the (1R*,5S*,8R*)-8-(tert-butoxycarbonylamino)-2-axa-6-azabicyclo[3.3.0] octane obtained in Example A, 1.75 g of 5-amino-1-cyclopropyl-6,7,8-trifluoro-1,4-dihydro-4-oxoquinoline-3-carboxylic acid, 920 mg of 1,8-diazabicyclo[5.4.0]-7-undecene (DBU), and 17 ml of pyridine was heated at 60° C. for 16 hours and then at 80° C. for 5 hours. After the solvent was distilled off under reduced pressure, the resulting residue was dissolved in chloroform. This solution was washed with cold dilute hydrochloric acid and then with a saturated solution of sodium chloride, and dried over anhydrous magnesium sulfate. The solvent was distilled off under reduced pressure to obtain an oily material.

(2) A mixture composed of the oily material obtained in the preceding step (1), 3.5 ml of a 10% aqueous solution of hydrochloric acid, and 9 ml of tetrahydrofuran was heated at 80° C. for 2 hours, and the solvent was distilled off under reduced pressure. Then, 10 ml of water and 8 ml of a 10% aqueous solution of hydrochloric acid were added to the resulting residue, and this mixture was filtered. The filtrate was washed three times with 10 ml portions of chloroform, alkalified by the addition of a 10% aqueous solution of sodium hydroxide, and further washed three times with chloroform. Thereafter, the filtrate was adjusted to pH 8–9 with a 10% aqueous solution of hydrochloric acid, and then extracted with chloroform. After the extract was dried over anhydrous sodium sulfate, the solvent was distilled off under reduced pressure to obtain crude crystals. These crystals were recrystallized from methylene chloride-ethyl acetate to obtain 111 mg of the desired title compound.

Melting point: 258–263° C. (dec.).

Examples 4–38

The following compounds were obtained in substantially the same manner as described in Example 1 or 3.

TABLE 3

| Example | A | R | X | W | n' | B | m.p. (° C.) |
|---|---|---|---|---|---|---|---|
| 4 | C—OMe | cyclopropyl | NH₂ | H₂N⁞⁞⁞⁞ | 1 | — | 253–257 (dec.) |
| 5 | C—OMe | cyclopropyl | Me | H₂N⁞⁞⁞⁞ | 1 | 0.5 HCl | 244–247 (dec.) |
| 6 | C—OMe | cyclopropyl | H | MeHN⁞⁞⁞⁞ | 1 | — | 201–203 |
| 7 | C—OMe | F-cyclopropyl (cis) | H | H₂N⁞⁞⁞⁞ | 1 | — | 121–125 |
| 8 | C—OMe | cyclopropyl | Me | MeHN⁞⁞⁞⁞ | 1 | — | 194–196 |
| 9 | C—OMe | cyclopropyl | NH₂ | MeHN⁞⁞⁞⁞ | 1 | — | 227–230 |
| 10 | C—OMe | cyclopropyl | H | H₂N⁞⁞⁞⁞ | 2 | — | 205–208 |
| 11 | N | 2,4-F₂Ph | H | H₂N⁞⁞⁞⁞ | 1 | — | 144–146 |

TABLE 4
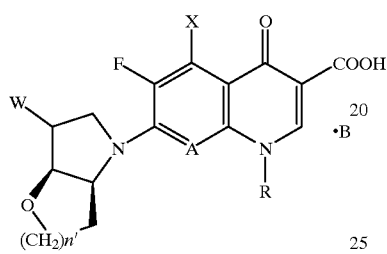
| Example | A | R | X | W | n' | B | m.p. (° C.) |
|---|---|---|---|---|---|---|---|
| 12 | C—OMe | cyclopropyl | NH₂ | H₂N╍╍╍ | 2 | — | 253–255 (dec.) |
| 13 | C—OMe | cyclopropyl | NH₂ | H₂N▶ | 1 | — | 260–263 (dec.) |
| 14 | C—OCHF₂ | cyclopropyl | H | H₂N╍╍╍ | 1 | — | 182–185 |
| 15 | C—Cl | cyclopropyl | H | H₂N╍╍╍ | 1 | — | 130–135 |
| 16 | C—OMe | cyclopropyl | Me | H₂N▶ | 1 | — | 230–233 (dec.) |
| 17 | N | 2,4-F₂Ph | H | MeHN╍╍╍ | 1 | 0.1 HCl | 153–155 |
| 18 | CF | cyclopropyl | H | H₂N╍╍╍ | 1 | 0.1 HCl | 218–223 |
| 19 | C—OMe | cyclopropyl | H | H₂N▶ | 2 | — | 196–198 |

TABLE 5
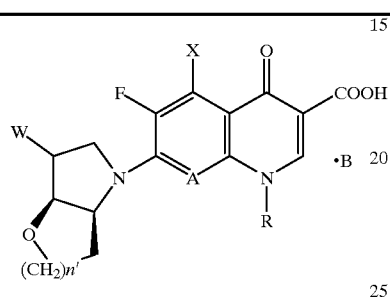
| Example | A | R | X | W | n' | B | m.p. (° C.) |
|---|---|---|---|---|---|---|---|
| 20 | C—Cl | cyclopropyl | H | MeHN⋯ | 1 | — | 105–110 (dec.) |
| 21 | C—F | cyclopropyl | NH₂ | H₂N▬ | 2 | — | 245–248 |
| 22 | N | cyclopropyl | H | H₂N⋯ | 1 | — | 230–233 (dec.) |
| 23 | C—OMe | cyclopropyl | H | H₂N▬ | 1 | — | 199–201 |
| 24 | C—Me | cyclopropyl | Me | H₂N⋯ | 1 | — | 205–213 (dec.) |
| 25 | C—Cl | fluorocyclopropyl (cis) | H | H₂N⋯ | 1 | — | 144–148 |
| 26 | CH | cyclopropyl | H | H₂N⋯ | 1 | — | 233–238 (dec.) |
| 27 | C—C≡CH | cyclopropyl | H | H₂N⋯ | 1 | — | 232–234 (dec.) |

TABLE 6

| Example | A | R | X | W | n' | B | m.p. (° C.) |
|---|---|---|---|---|---|---|---|
| 28 | C—OMe | (1R, 2S) cyclopropyl-F | H | MeHN‖‖‖ | 1 | — | 143–146 |
| 29 | N | 2,4-F₂Ph | H | H₂N▶ | 1 | HCl | 258–261 (dec.) |
| 30 | C—CN | cyclopropyl | Me | H₂N▶ | 2 | — | 260–265 |
| 31 | C—OMe | cyclopropyl-F (cis) | H | H₂N▶ | 1 | — | 202–205 (dec.) |
| 32 | C—OMe | cyclopropyl | NH₂ | H₂N▶ | 2 | — | 272–276 (dec.) |
| 33 | C—CH=CH₂ | cyclopropyl | H | H₂N‖‖‖ | 1 | — | 218–221 |
| 34 | C—CN | cyclopropyl | H | H₂N▶ | 2 | — | 223–226 |
| 35 | C—OMe | cyclopropyl | H | MeHN▶ | 1 | — | 174–177 |

TABLE 7

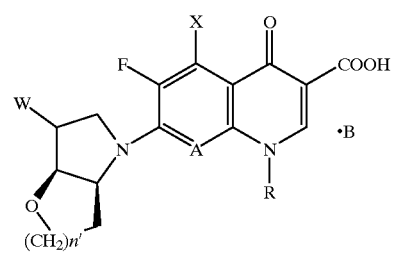

| Example | A | R | X | W | n' | B | m.p. (° C.) |
|---|---|---|---|---|---|---|---|
| 36 | C—OMe | ▷ | Me | H₂N▬ | 2 | — | 205–208 |
| 37 | C—OCHF₂ | ▷ | H | H₂N▬ | 1 | — | 193–196 |
| 38 | C—CN | ▷ | H | H₂N┉ | 1 | — | 144–148 |

Example 39

The following compound was obtained in substantially the same manner as in Example 3.

7-[(1R*,5R*,8S*)-8-amino-2-oxa-6-azabicyclo[3.3.0]oct-6-yl]-6-fluoro-1-(2,4-difluorophenyl)-1,4-dihydro-5-methyl-4-oxo-1,8-naphthyridine-3-carboxylic acid.

Melting point: 224–227° C. (dec.).

Example 40

The following compound was obtained in substantially the same manner as in Example 1.

7-[(1R*,5R*,8R*)-8-amino-3-methyl-2-oxa-6-azabicyclo[3.3.0]oct-6-yl]-1-cyclopropyl-6-fluoro-1,4-dihydro-8-methoxy-4-oxoquinoline-3-carboxylic acid.

Melting point: 166–168° C.

Example 41

The following compound was obtained in substantially the same manner as in Example 1.

10-[(1R*,5R*,8S*)-8-amino-2-oxa-6-azabicyclo[3.3.0]oct-6-yl]-9-fluoro-2,3-dihydro-(3S)-3-methyl-7-oxo-7H-pyrido[1,2,3-de][1,4]benzoxazine-6-carboxylic acid.

Melting point: 231–233° C.

Example 42

The following compound was obtained in substantially the same manner as in Example 3.

7-[(1R*,5R*,8R*)-8-amino-2-oxa-6-azabicyclo[3.3.0]oct-6-yl]-1-cyclopropyl-6-fluoro-1,4-dihydro-4-oxoquinoline-3-carboxylic acid.

Melting point: 238–241° C. (dec.).

Example 43

The following compound was obtained in substantially the same manner as in Example 1.

7-[(1R*,5R*,8S*)-8-amino-2-oxa-6-azabicyclo-[3.3.0]oct-6-yl]-1-cyclopropyl-6-fluoro-1,4-dihydro-8-methylthio-4-oxoquinoline-3-carboxylic acid.

Melting point: 226–228° C. (dec.).

Example 44

The following compound was obtained in substantially the same manner as in Example 3.

1-(3-Amino-4,6-difluorophenyl)-7-[(1R*,5R*,8S*)-8-amino-2-oxa-6-azabicyclo[3.3.0]oct-6-yl]-6-fluoro-1,4-dihydro-4-oxo-1,8-naphthyridine-3-carboxylic acid.

Melting point: 160–163° C.

Example 45

The following compound was obtained in substantially the same manner as in Example 1.

7-[(1R*,5R*,8S*)-8-amino-3-methyl-2-oxa-6-azabicyclo[3.3.0]oct-6-yl]-1-cyclopropyl-6-fluoro-1,4-dihydro-8-methoxy-4-oxoquinoline-3-carboxylic acid.

Melting point: 109–112° C.

Example 46

The following compound was obtained in substantially the same manner as in Example 3.

7-[(1R*,5R*)-8-aminomethyl-2-oxa-6-azabicyclo[3.3.0]oct-6-yl]-6-fluoro-1-(2,4-difluorophenyl)-1,4-dihydro-4-oxo-1,8-naphthyridine-3-carboxylic acid.

Melting point: 230–233° C.

Example 47

The following compound was obtained in substantially the same manner as in Example 3.

5-Amino-7-[(1R*,5R*,8S*)-8-amino-2-oxa-6-azabicyclo[3.3.0]oct-6-yl]-6-fluoro-1-(2,4-difluorophenyl)-1,4-dihydro-4-oxo-1,8-naphthyridine-3-carboxylic acid.

Example 48

The following compound was obtained in substantially the same manner as in Example 1.

5-Amino-7-[(1R*,5R*,8S*)-8-amino-2-oxa-6-azabicyclo[3.3.0]oct-6-yl]-6-fluoro-1-[(1R,2S)-2-fluorocyclopropyl]-1,4-dihydro-8-methoxy-4-oxoquinoline-3-carboxylic acid.

Example N
Preparation of Tablets

| | |
|---|---|
| Compound of Example 1 | 250 g |
| Corn starch | 54 g |
| Carboxymethylcellulose Ca | 40 g |
| Microcrystalline cellulose | 50 g |
| Magnesium stearate | 6 g |

The above ingredients were blended together with ethanol. The resulting blend was granulated and tableted in the usual manner. Thus, there were obtained 2,000 tablets each weighing 200 mg.

INDUSTRIAL APPLICABILITY

As described above, the compounds (I) of the present invention are useful as antibacterial agents for human beings and other animals. Moreover, the bicyclic compounds (II) of the present invention are useful as direct intermediates for the synthesis of the compounds (I) of the present invention.

We claim:

1. A pyridonecarboxylic acid compound of the following formula (I):

(I)

or an ester or salt thereof,
wherein:
R represents a lower alkyl group, a lower alkenyl group or a lower cycloalkyl group each of which may optionally be substituted by one or more halogen atoms, or R represents a phenyl group which may optionally be substituted by one or more halogen atoms and/or an amino group;

X represents a hydrogen atom, a halogen atom, a hydroxyl group, a lower alkyl group, a lower alkoxy group or an amino group which may be protected;

Y represents a hydrogen atom or a halogen atom;

A represents a nitrogen atom or a group of the formula c—Z in which Z represents a hydrogen atom, a halogen atom, or a cyano group, or Z represents a lower alkoxy group, a lower alkyl group, a lower alkylthio group, a lower alkenyl group or a lower alkynyl group each of which may optionally be substituted by one or more halogen atoms, or A combines with R to form a bridge represented by the formula —O—$CH_2$—CH($CH_3$)—;

$R_1$ and $R_2$ are the same or different and each represent a hydrogen atom, a lower alkyl group or an amino-protecting group;

$R_3$ represents a hydrogen atom or a lower alkyl group;

$R_4$, $R_5$, $R_6$, $R_7$, $R_8$ and $R_9$ are the same or different and each represent a hydrogen atom, a halogen atom or a lower alkyl group;

m is 0 or 1; and n and p are the same or different and are each 0 or 1.

2. A pyridonecarboxylic acid compound, ester or salt thereof as claimed in claim 1 wherein n is 1.

3. A pyridonecarboxylic acid compound, ester or salt thereof as claimed in claim 1 wherein R is a lower cycloalkyl group which may optionally be substituted by one or more halogen atoms, or R is a phenyl group which is substituted by one or more halogen atoms and/or an amino group.

4. A pyridonecarboxylic acid compound, ester or salt thereof as claimed in claim 1 wherein X is a hydrogen atom, a lower alkyl group or an amino group.

5. A pyridonecarboxylic acid compound, ester or salt thereof as claimed in claim 1 wherein Y is a fluorine atom.

6. A pyridonecarboxylic acid compound, ester or salt thereof as claimed in claim 1 wherein A is a nitrogen atom or c—Z in which Z is a hydrogen atom, a halogen atom, a cyano group, or Z is a lower alkoxy, lower alkyl, lower alkylthio, lower alkenyl or lower alkynyl group that may optionally be substituted by one or more halogen atoms.

7. A pyridonecarboxylic acid compound, ester or salt thereof as claimed in claim 1 wherein $R_1$ and $R_2$ are the same or different and are each a hydrogen atom or a lower alkyl group.

8. A pyridonecarboxylic acid compound, ester or salt thereof as claimed in claim 1 wherein $R_3$ is a hydrogen atom.

9. A pyridonecarboxylic acid compound, ester or salt thereof as claimed in claim 1 wherein $R_4$, $R_5$, $R_6$, $R_7$, $R_8$ and $R_9$ are the same or different and are each a hydrogen atom or a lower alkyl group.

10. A pyridonecarboxylic acid compound, ester or salt thereof as claimed in claim 1 wherein R is a cyclopropyl, 2-fluorocyclopropyl, 2,4-difluorophenyl or 3-amino-4,6-difluorophenyl group; X is a hydrogen atom, a methyl group or an amino group; Y is a fluorine atom; A is a nitrogen atom or c—Z in which Z is a hydrogen atom, a fluorine atom, a chlorine atom, a cyano group, a methoxy group, a difluoromethoxy group, a methyl group, a methylthio group, a vinyl group or an ethynyl group; $R_1$ and $R_2$ are the same or different and are each a hydrogen atom or a methyl group; $R_3$ is a hydrogen atom; $R_4$, $R_5$, $R_6$, $R_7$, $R_8$ and $R_9$ are the same or different and are each a hydrogen atom or a methyl group; and n is 1.

11. A bicyclic amine compound of the following formula (II):

(II)

of a salt thereof,
wherein:
$R_1$ and $R_2$ are the same or different and each represent a hydrogen atom, a lower alkyl group or an amino-protecting group;

$R_3$ represents a hydrogen atom or a lower alkyl group;

$R_4$, $R_5$, $R_6$, $R_7$, $R_8$ and $R_9$ are the same or different and each represent a hydrogen atom, a halogen atom or a lower alkyl group;

m is 0 or 1; and n and p are the same or different and are each 0 or 1.

12. A bicyclic amine compound or an acid addition salt thereof as claimed in claim 11 wherein $R_1$ and $R_2$ are the same or different and are each a hydrogen atom, a lower alkyl group, or an amino-protecting group which can be eliminated by hydrolysis; $R_3$ is a hydrogen atom; $R_4$, $R_5$, $R_6$, $R_7$, $R_8$ and $R_9$ are the same or different and are each a hydrogen atom or a lower alkyl group; and n is 1.

13. A bicyclic amine compound or an acid addition salt thereof as claimed in claim 11 wherein $R_1$ and $R_2$ are the same or different and are each a hydrogen atom, a methyl group, a tert-butoxycarbonyl group or a trifluoroacetyl group; $R_3$ is a hydrogen atom; $R_4$, $R_5$, $R_6$, $R_7$, $R_8$ and $R_9$ are the same or different and are each a hydrogen atom or a methyl group; and n is 1.

14. A pharmaceutical composition comprising, as an active ingredient, a pyridonecarboxylic acid compound as claimed in claim 1, an ester thereof or a physiologically acceptable salt thereof.

15. A method for the treatment of a bacterial disease in a mammal, which comprises administering an antibacterially effective amount of a pyridonecarboxylic acid compound as claimed in claim 1, an ester thereof or a physiologically acceptable salt thereof to the mammal in need thereof.

* * * * *